(12) United States Patent
Tabor et al.

(10) Patent No.: US 7,972,378 B2
(45) Date of Patent: Jul. 5, 2011

(54) STENTS FOR PROSTHETIC HEART VALVES

(75) Inventors: Charles Tabor, St. Louis Park, MN (US); Carol E. Eberhardt, Fullerton, CA (US); Timothy G. Laske, Shoreview, MN (US); Timothy R. Ryan, Shorewood, MN (US); Joseph C. Morrow, Eden Prairie, MN (US); Tammy Y. Tam, San Francisco, CA (US); Brian A. Glynn, Santa Rosa, CA (US); Anne L. Brody Rubin, San Francisco, CA (US); J. Michael Tuchek, Berwyn, IL (US)

(73) Assignee: Medtronic, Inc., Minneapolis, MN (US)

( * ) Notice: Subject to any disclaimer, the term of this patent is extended or adjusted under 35 U.S.C. 154(b) by 57 days.

(21) Appl. No.: 12/321,760

(22) Filed: Jan. 23, 2009

(65) Prior Publication Data
US 2009/0287299 A1  Nov. 19, 2009

Related U.S. Application Data

(60) Provisional application No. 61/062,207, filed on Jan. 24, 2008, provisional application No. 61/075,902, filed on Jun. 26, 2008.

(51) Int. Cl.
*A61F 2/24* (2006.01)
*A61F 2/06* (2006.01)
(52) U.S. Cl. .................... 623/2.17; 623/1.24
(58) Field of Classification Search .............. 623/1.24, 623/2.17–2.18
See application file for complete search history.

(56) References Cited

U.S. PATENT DOCUMENTS

| | | | |
|---|---|---|---|
| 3,334,629 A | 8/1967 | Cohn | |
| 3,409,013 A | 11/1968 | Berry | |
| 3,540,431 A | 11/1970 | Mobin-Uddin | |
| 3,587,115 A | 6/1971 | Shiley | |
| 3,628,535 A | 12/1971 | Ostrowsky et al. | |
| 3,642,004 A | 2/1972 | Osthagen et al. | |
| 3,657,744 A | 4/1972 | Ersek | |
| 3,671,979 A | 6/1972 | Moulopoulos | |
| 3,714,671 A | 2/1973 | Edwards et al. | |
| 3,755,823 A | 9/1973 | Hancock | |

(Continued)

FOREIGN PATENT DOCUMENTS

CN  2007-100074433  1/2007

(Continued)

OTHER PUBLICATIONS

Andersen. H.R. et al. "Transluminal implantation of artificial heart valves. Description of a new expandable aortic valve and initial results with implantation by catheter technique in closed chest pigs." Euro. Heart J. (1992) 13:704-708.

(Continued)

*Primary Examiner* — Suzette J Gherbi

(57) ABSTRACT

A stented valve including a stent structure including a generally tubular body portion that has a first end and a second end, wherein an area adjacent the first end has a first stiffness, an area adjacent the second end has a second stiffness, and a central region between the areas at the first and second ends has a third stiffness that is less than the stiffness adjacent the first and second ends, wherein the stent structure can be reconfigured in its central area to match a curved patient anatomical region. The stented valve further includes a valve structure attached within the generally tubular portion.

11 Claims, 17 Drawing Sheets

U.S. PATENT DOCUMENTS

| | | |
|---|---|---|
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos |
| 4,291,420 A | 9/1981 | Reul |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,425,908 A | 1/1984 | Simon |
| 4,470,157 A | 9/1984 | Love |
| 4,501,030 A | 2/1985 | Lane |
| 4,506,394 A | 3/1985 | Bedard |
| 4,574,803 A | 3/1986 | Storz |
| 4,580,568 A | 4/1986 | Gianturco |
| 4,592,340 A | 6/1986 | Boyles |
| 4,610,688 A | 9/1986 | Silvestrini et al. |
| 4,612,011 A | 9/1986 | Kautzky |
| 4,647,283 A | 3/1987 | Carpentier et al. |
| 4,648,881 A | 3/1987 | Carpentier et al. |
| 4,655,771 A | 4/1987 | Wallsten |
| 4,662,885 A | 5/1987 | DiPisa, Jr. |
| 4,665,906 A | 5/1987 | Jervis |
| 4,681,908 A | 7/1987 | Broderick et al. |
| 4,710,192 A | 12/1987 | Liotta et al. |
| 4,733,665 A | 3/1988 | Palmaz |
| 4,777,951 A | 10/1988 | Cribier et al. |
| 4,787,899 A | 11/1988 | Lazarus |
| 4,796,629 A | 1/1989 | Grayzel |
| 4,797,901 A | 1/1989 | Baykut |
| 4,819,751 A | 4/1989 | Shimada et al. |
| 4,834,755 A | 5/1989 | Silvestrini et al. |
| 4,856,516 A | 8/1989 | Hillstead |
| 4,872,874 A | 10/1989 | Taheri |
| 4,878,495 A | 11/1989 | Grayzel |
| 4,878,906 A | 11/1989 | Lindemann et al. |
| 4,883,458 A | 11/1989 | Shiber |
| 4,909,252 A | 3/1990 | Goldberger |
| 4,917,102 A | 4/1990 | Miller et al. |
| 4,922,905 A | 5/1990 | Strecker |
| 4,954,126 A | 9/1990 | Wallsten |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,061,273 A | 10/1991 | Yock |
| 5,085,635 A | 2/1992 | Cragg |
| 5,089,015 A | 2/1992 | Ross |
| 5,152,771 A | 10/1992 | Sabbaghian et al. |
| 5,161,547 A | 11/1992 | Tower |
| 5,163,953 A | 11/1992 | Vince |
| 5,167,628 A | 12/1992 | Boyles |
| 5,217,483 A | 6/1993 | Tower |
| 5,232,445 A | 8/1993 | Bonzel |
| 5,272,909 A | 12/1993 | Nguyen et al. |
| 5,295,958 A | 3/1994 | Shturman |
| 5,327,774 A | 7/1994 | Nguyen et al. |
| 5,332,402 A | 7/1994 | Teitelbaum et al. |
| 5,350,398 A | 9/1994 | Pavcnik et al. |
| 5,370,685 A | 12/1994 | Stevens |
| 5,389,106 A | 2/1995 | Tower |
| 5,397,351 A | 3/1995 | Pavcnik et al. |
| 5,411,552 A | 5/1995 | Andersen et al. |
| 5,415,633 A | 5/1995 | Lazarus et al. |
| 5,431,676 A | 7/1995 | Dubrul et al. |
| 5,443,446 A | 8/1995 | Shturman |
| 5,449,384 A | 9/1995 | Johnson |
| 5,480,424 A | 1/1996 | Cox |
| 5,489,294 A | 2/1996 | McVenes et al. |
| 5,489,297 A | 2/1996 | Duran |
| 5,496,346 A | 3/1996 | Horzewski et al. |
| 5,500,014 A | 3/1996 | Quijano et al. |
| 5,507,767 A | 4/1996 | Maeda et al. |
| 5,545,209 A | 8/1996 | Roberts et al. |
| 5,545,211 A | 8/1996 | An et al. |
| 5,545,214 A | 8/1996 | Stevens |
| 5,554,185 A | 9/1996 | Block et al. |
| 5,575,818 A | 11/1996 | Pinchuk |
| 5,580,922 A | 12/1996 | Park et al. |
| 5,591,195 A | 1/1997 | Taheri et al. |
| 5,609,626 A | 3/1997 | Quijano et al. |
| 5,645,559 A | 7/1997 | Hachtman et al. |
| 5,665,115 A | 9/1997 | Cragg |
| 5,667,523 A | 9/1997 | Bynon et al. |
| 5,674,277 A | 10/1997 | Freitag |
| 5,695,498 A | 12/1997 | Tower |
| 5,702,368 A | 12/1997 | Stevens et al. |
| 5,713,953 A | 2/1998 | Vallana et al. |
| 5,716,417 A | 2/1998 | Girard et al. |
| 5,746,709 A | 5/1998 | Rom et al. |
| 5,749,890 A | 5/1998 | Shaknovich |
| 5,766,151 A | 6/1998 | Valley et al. |
| 5,782,809 A | 7/1998 | Umeno et al. |
| 5,800,456 A | 9/1998 | Maeda et al. |
| 5,800,508 A | 9/1998 | Goicoechea et al. |
| 5,817,126 A | 10/1998 | Imran |
| 5,824,041 A | 10/1998 | Lenker |
| 5,824,043 A | 10/1998 | Cottone, Jr. |
| 5,824,053 A | 10/1998 | Khosravi et al. |
| 5,824,056 A | 10/1998 | Rosenberg |
| 5,824,061 A | 10/1998 | Quijano et al. |
| 5,824,064 A | 10/1998 | Taheri |
| 5,840,081 A | 11/1998 | Andersen et al. |
| 5,843,158 A | 12/1998 | Lenker et al. |
| 5,851,232 A | 12/1998 | Lois |
| 5,855,597 A | 1/1999 | Jayaraman |
| 5,855,601 A | 1/1999 | Bessler et al. |
| 5,860,996 A | 1/1999 | Urban et al. |
| 5,861,028 A | 1/1999 | Angell |
| 5,868,783 A | 2/1999 | Tower |
| 5,876,448 A | 3/1999 | Thompson et al. |
| 5,888,201 A | 3/1999 | Stinson et al. |
| 5,891,191 A | 4/1999 | Stinson |
| 5,906,619 A | 5/1999 | Olson et al. |
| 5,907,893 A | 6/1999 | Zadno-Azizi et al. |
| 5,913,842 A | 6/1999 | Boyd et al. |
| 5,925,063 A | 7/1999 | Khosravi |
| 5,944,738 A | 8/1999 | Amplatz et al. |
| 5,957,949 A | 9/1999 | Leonhardt et al. |
| 5,968,068 A | 10/1999 | Dehdashtian et al. |
| 5,984,957 A | 11/1999 | Laptewicz, Jr. et al. |
| 5,997,573 A | 12/1999 | Quijano et al. |
| 6,022,370 A | 2/2000 | Tower |
| 6,027,525 A | 2/2000 | Suh et al. |
| 6,029,671 A | 2/2000 | Stevens et al. |
| 6,042,589 A | 3/2000 | Marianne |
| 6,042,598 A | 3/2000 | Tsugita et al. |
| 6,042,607 A | 3/2000 | Williamson, IV |
| 6,051,104 A | 4/2000 | Jang |
| 6,059,809 A | 5/2000 | Amor et al. |
| 6,110,201 A | 8/2000 | Quijano et al. |
| 6,146,366 A | 11/2000 | Schachar |
| 6,159,239 A | 12/2000 | Greenhalgh |
| 6,162,208 A | 12/2000 | Hipps |
| 6,162,245 A | 12/2000 | Jayaraman |
| 6,168,614 B1 | 1/2001 | Andersen et al. |
| 6,171,335 B1 | 1/2001 | Wheatley et al. |
| 6,200,336 B1 | 3/2001 | Pavcnik et al. |
| 6,203,550 B1 | 3/2001 | Olson |
| 6,210,408 B1 | 4/2001 | Chandrasekaran et al. |
| 6,218,662 B1 | 4/2001 | Tchakarov et al. |
| 6,221,006 B1 | 4/2001 | Dubrul et al. |
| 6,221,091 B1 | 4/2001 | Khosravi |
| 6,241,757 B1 | 6/2001 | An et al. |

| Patent | Date | Name | | Patent | Date | Name |
|---|---|---|---|---|---|---|
| 6,245,102 B1 | 6/2001 | Jayaraman | | 6,866,650 B2 | 3/2005 | Stevens |
| 6,248,116 B1 | 6/2001 | Chevilon | | 6,872,223 B2 | 3/2005 | Roberts |
| 6,258,114 B1 | 7/2001 | Konya et al. | | 6,875,231 B2 | 4/2005 | Anduiza et al. |
| 6,258,115 B1 | 7/2001 | Dubrul | | 6,883,522 B2 | 4/2005 | Spence et al. |
| 6,258,120 B1 | 7/2001 | McKenzie et al. | | 6,887,266 B2 | 5/2005 | Williams et al. |
| 6,277,555 B1 | 8/2001 | Duran et al. | | 6,890,330 B2 | 5/2005 | Streeter et al. |
| 6,299,637 B1 * | 10/2001 | Shaolian et al. ............. 623/1.24 | | 6,893,460 B2 | 5/2005 | Spenser et al. |
| 6,302,906 B1 | 10/2001 | Goicoechea et al. | | 6,896,690 B1 | 5/2005 | Lambrecht et al. |
| 6,309,382 B1 | 10/2001 | Garrison et al. | | 6,908,481 B2 | 6/2005 | Cribier |
| 6,309,417 B1 | 10/2001 | Spence et al. | | 6,913,600 B2 | 7/2005 | Valley et al. |
| 6,338,735 B1 | 1/2002 | Stevens | | 6,929,653 B2 | 8/2005 | Strecter |
| 6,348,063 B1 | 2/2002 | Yassour et al. | | 6,936,066 B2 | 8/2005 | Palmaz et al. |
| 6,350,277 B1 | 2/2002 | Kocur | | 6,939,365 B1 | 9/2005 | Fogarty et al. |
| 6,352,708 B1 | 3/2002 | Duran et al. | | 6,951,571 B1 | 10/2005 | Srivastava |
| 6,371,970 B1 | 4/2002 | Khosravi et al. | | 6,974,474 B2 | 12/2005 | Pavcnik et al. |
| 6,371,983 B1 | 4/2002 | Lane | | 6,974,476 B2 | 12/2005 | McGuckin et al. |
| 6,379,383 B1 | 4/2002 | Palmaz et al. | | 6,986,742 B2 | 1/2006 | Hart et al. |
| 6,380,457 B1 | 4/2002 | Yurek et al. | | 6,989,027 B2 | 1/2006 | Allen et al. |
| 6,398,807 B1 | 6/2002 | Chouinard et al. | | 6,989,028 B2 | 1/2006 | Lashinski et al. |
| 6,409,750 B1 | 6/2002 | Hyodoh et al. | | 6,991,649 B2 | 1/2006 | Sievers |
| 6,425,916 B1 | 7/2002 | Garrison et al. | | 7,018,401 B1 | 3/2006 | Hyodoh et al. |
| 6,440,164 B1 | 8/2002 | DiMatteo et al. | | 7,041,128 B2 | 5/2006 | McGuckin, Jr. et al. |
| 6,454,799 B1 | 9/2002 | Schreck | | 7,044,966 B2 | 5/2006 | Svanidze et al. |
| 6,458,153 B1 | 10/2002 | Bailey et al. | | 7,048,014 B2 | 5/2006 | Hyodoh et al. |
| 6,461,382 B1 | 10/2002 | Cao | | 7,097,659 B2 | 8/2006 | Woolfson et al. |
| 6,468,303 B1 | 10/2002 | Amplatz et al. | | 7,101,396 B2 | 9/2006 | Artof et al. |
| 6,475,239 B1 | 11/2002 | Campbell et al. | | 7,105,016 B2 | 9/2006 | Shiu et al. |
| 6,482,228 B1 | 11/2002 | Norred | | 7,115,141 B2 | 10/2006 | Menz et al. |
| 6,488,704 B1 | 12/2002 | Connelly et al. | | 7,128,759 B2 | 10/2006 | Osborne et al. |
| 6,494,909 B2 | 12/2002 | Greenhalgh | | 7,147,663 B1 | 12/2006 | Berg et al. |
| 6,503,272 B2 | 1/2003 | Duerig et al. | | 7,153,324 B2 | 12/2006 | Case et al. |
| 6,508,833 B2 | 1/2003 | Pavcnik et al. | | 7,160,319 B2 | 1/2007 | Chouinard et al. |
| 6,527,800 B1 | 3/2003 | McGuckin, Jr. et al. | | 7,175,656 B2 | 2/2007 | Khairkhahan |
| 6,530,949 B2 | 3/2003 | Konya et al. | | 7,186,265 B2 | 3/2007 | Sharkawy et al. |
| 6,530,952 B2 | 3/2003 | Vesely | | 7,195,641 B2 | 3/2007 | Palmaz et al. |
| 6,562,031 B2 | 5/2003 | Chandrasekaran et al. | | 7,198,646 B2 | 4/2007 | Figulla et al. |
| 6,562,058 B2 | 5/2003 | Seguin et al. | | 7,201,761 B2 | 4/2007 | Woolfson et al. |
| 6,569,196 B1 | 5/2003 | Vesely | | 7,201,772 B2 | 4/2007 | Schwammenthal et al. |
| 6,585,758 B1 | 7/2003 | Chouinard et al. | | 7,252,682 B2 | 8/2007 | Seguin |
| 6,592,546 B1 | 7/2003 | Barbut et al. | | 7,300,457 B2 | 11/2007 | Palmaz |
| 6,605,112 B1 | 8/2003 | Moll et al. | | 7,300,463 B2 | 11/2007 | Liddicoat |
| 6,613,077 B2 | 9/2003 | Gilligan et al. | | 7,316,706 B2 | 1/2008 | Bloom et al. |
| 6,622,604 B1 | 9/2003 | Chouinard et al. | | 7,329,278 B2 | 2/2008 | Seguin |
| 6,635,068 B1 | 10/2003 | Dubrul et al. | | 7,335,218 B2 | 2/2008 | Wilson et al. |
| 6,652,571 B1 | 11/2003 | White et al. | | 7,338,520 B2 | 3/2008 | Bailey et al. |
| 6,652,578 B2 | 11/2003 | Bailey et al. | | 7,351,256 B2 * | 4/2008 | Hojeibane et al. ............ 623/1.24 |
| 6,656,213 B2 | 12/2003 | Solem | | 7,374,571 B2 | 5/2008 | Pease et al. |
| 6,663,663 B2 | 12/2003 | Kim et al. | | 7,377,938 B2 | 5/2008 | Sarac et al. |
| 6,669,724 B2 | 12/2003 | Park et al. | | 7,381,218 B2 | 6/2008 | Schreck |
| 6,673,089 B1 | 1/2004 | Yassour et al. | | 7,384,411 B1 | 6/2008 | Condado |
| 6,673,109 B2 | 1/2004 | Cox | | 7,429,269 B2 | 9/2008 | Schwammenthal et al. |
| 6,676,698 B2 | 1/2004 | McGuckin, Jr. et al. | | 7,442,204 B2 | 10/2008 | Schwammenthal et al. |
| 6,682,558 B2 | 1/2004 | Tu et al. | | 7,462,191 B2 | 12/2008 | Spenser et al. |
| 6,682,559 B2 | 1/2004 | Myers et al. | | 7,470,284 B2 | 12/2008 | Lambrecht et al. |
| 6,685,739 B2 | 2/2004 | DiMatteo et al. | | 7,481,838 B2 | 1/2009 | Carpentier et al. |
| 6,689,144 B2 | 2/2004 | Gerberding | | 7,544,206 B2 | 6/2009 | Cohn et al. |
| 6,689,164 B1 | 2/2004 | Seguin | | 7,547,322 B2 * | 6/2009 | Sarac et al. ................. 623/1.24 |
| 6,692,512 B2 | 2/2004 | Jang | | 7,556,646 B2 | 7/2009 | Yang et al. |
| 6,692,513 B2 | 2/2004 | Streeter et al. | | 7,569,071 B2 * | 8/2009 | Haverkost et al. ........... 623/1.24 |
| 6,695,878 B2 | 2/2004 | McGuckin, Jr. et al. | | 7,618,447 B2 * | 11/2009 | Case et al. ................... 623/1.26 |
| 6,702,851 B1 | 3/2004 | Chinn et al. | | 7,682,390 B2 | 3/2010 | Seguin |
| 6,719,789 B2 | 4/2004 | Cox | | 7,780,726 B2 | 8/2010 | Seguin |
| 6,730,118 B2 | 5/2004 | Spenser et al. | | 7,806,919 B2 | 10/2010 | Bloom et al. |
| 6,730,377 B2 | 5/2004 | Wang | | 2001/0002445 A1 | 3/2001 | Vesely |
| 6,733,525 B2 | 5/2004 | Yang et al. | | 2001/0001314 A1 | 5/2001 | Davison et al. |
| 6,736,846 B2 | 5/2004 | Cox | | 2001/0007956 A1 | 7/2001 | Letac et al. |
| 6,752,828 B2 | 6/2004 | Thornton | | 2001/0010017 A1 | 7/2001 | Letac et al. |
| 6,758,855 B2 | 7/2004 | Fulton, III et al. | | 2001/0011189 A1 | 8/2001 | Drasler et al. |
| 6,769,434 B2 | 8/2004 | Liddicoat et al. | | 2001/0021872 A1 | 9/2001 | Bailey et al. |
| 6,786,925 B1 | 9/2004 | Schoon | | 2001/0025196 A1 | 9/2001 | Chinn et al. |
| 6,790,229 B1 | 9/2004 | Berreklouw | | 2001/0032013 A1 | 10/2001 | Marton |
| 6,790,230 B2 | 9/2004 | Beyersdorf et al. | | 2001/0039450 A1 | 11/2001 | Pavcnik et al. |
| 6,792,979 B2 | 9/2004 | Konya et al. | | 2001/0041928 A1 | 11/2001 | Pavcnik et al. |
| 6,797,002 B2 | 9/2004 | Spence | | 2001/0044647 A1 | 11/2001 | Pinchuk et al. |
| 6,821,297 B2 | 11/2004 | Snyders | | 2002/0010508 A1 | 1/2002 | Chobotov |
| 6,830,575 B2 | 12/2004 | Stenzel et al. | | 2002/0029014 A1 | 3/2002 | Jayaraman |
| 6,830,584 B1 | 12/2004 | Seguin | | 2002/0032480 A1 | 3/2002 | Spence et al. |
| 6,830,585 B1 | 12/2004 | Artof | | 2002/0032481 A1 * | 3/2002 | Gabbay ........................ 623/2.11 |
| 6,846,325 B2 | 1/2005 | Liddicoat | | 2002/0035396 A1 | 3/2002 | Heath |

| | | |
|---|---|---|
| 2002/0042650 A1 | 4/2002 | Vardi et al. |
| 2002/0052651 A1 | 5/2002 | Myers et al. |
| 2002/0058995 A1 | 5/2002 | Stevens |
| 2002/0072789 A1 | 6/2002 | Hackett et al. |
| 2002/0095209 A1 | 7/2002 | Zadno-Azizi et al. |
| 2002/0099439 A1 | 7/2002 | Schwartz et al. |
| 2002/0103533 A1 | 8/2002 | Langberg et al. |
| 2002/0107565 A1 | 8/2002 | Greenhalgh |
| 2002/0111674 A1 | 8/2002 | Chouinard et al. |
| 2002/0123802 A1 | 9/2002 | Snyders |
| 2002/0133183 A1 | 9/2002 | Lentz et al. |
| 2002/0138138 A1 | 9/2002 | Yang |
| 2002/0151970 A1 | 10/2002 | Garrison et al. |
| 2002/0161392 A1 | 10/2002 | Dubrul |
| 2002/0161394 A1 | 10/2002 | Macoviak et al. |
| 2002/0193871 A1 | 12/2002 | Beyersdorf et al. |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0028247 A1 | 2/2003 | Cali |
| 2003/0036791 A1 | 2/2003 | Bonhoeffer et al. |
| 2003/0040771 A1 | 2/2003 | Hyodoh et al. |
| 2003/0040772 A1 | 2/2003 | Hyodoh et al. |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0069492 A1 | 4/2003 | Abrams et al. |
| 2003/0109924 A1 | 6/2003 | Cribier |
| 2003/0125795 A1 | 7/2003 | Pavcnik et al. |
| 2003/0130726 A1 | 7/2003 | Thorpe et al. |
| 2003/0130729 A1 | 7/2003 | Paniagua et al. |
| 2003/0139804 A1 | 7/2003 | Hankh et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0181850 A1 | 9/2003 | Diamond et al. |
| 2003/0191519 A1 | 10/2003 | Lombardi et al. |
| 2003/0199913 A1 | 10/2003 | Dubrul et al. |
| 2003/0199963 A1 | 10/2003 | Tower et al. |
| 2003/0199971 A1 | 10/2003 | Tower et al. |
| 2003/0199975 A1* | 10/2003 | Gabbay ................ 623/2.36 |
| 2003/0212410 A1 | 11/2003 | Stenzel et al. |
| 2003/0212454 A1 | 11/2003 | Scott et al. |
| 2003/0225445 A1 | 12/2003 | Derus et al. |
| 2004/0019374 A1 | 1/2004 | Hojeibane et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0082904 A1 | 4/2004 | Houde et al. |
| 2004/0088045 A1 | 5/2004 | Cox |
| 2004/0092858 A1 | 5/2004 | Wilson et al. |
| 2004/0092989 A1 | 5/2004 | Wilson et al. |
| 2004/0093005 A1 | 5/2004 | Durcan |
| 2004/0093060 A1 | 5/2004 | Seguin et al. |
| 2004/0093075 A1 | 5/2004 | Kuehn |
| 2004/0097788 A1 | 5/2004 | Mourlas et al. |
| 2004/0098112 A1 | 5/2004 | DiMatteo et al. |
| 2004/0106976 A1 | 6/2004 | Bailey et al. |
| 2004/0106990 A1 | 6/2004 | Spence et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122514 A1 | 6/2004 | Fogarty et al. |
| 2004/0122516 A1 | 6/2004 | Fogarty |
| 2004/0127979 A1 | 7/2004 | Wilson |
| 2004/0138742 A1 | 7/2004 | Myers et al. |
| 2004/0138743 A1 | 7/2004 | Myers et al. |
| 2004/0153146 A1 | 8/2004 | Lashinski et al. |
| 2004/0167573 A1 | 8/2004 | Williamson |
| 2004/0167620 A1 | 8/2004 | Ortiz |
| 2004/0186563 A1 | 9/2004 | Iobbi |
| 2004/0193261 A1 | 9/2004 | Berreklouw |
| 2004/0210240 A1 | 10/2004 | Saint |
| 2004/0210304 A1 | 10/2004 | Seguin et al. |
| 2004/0210307 A1 | 10/2004 | Khairkhahan |
| 2004/0215333 A1 | 10/2004 | Duran |
| 2004/0215339 A1 | 10/2004 | Drasler et al. |
| 2004/0225353 A1 | 11/2004 | McGuckin, Jr. |
| 2004/0225354 A1 | 11/2004 | Allen |
| 2004/0254636 A1 | 12/2004 | Flagle et al. |
| 2004/0260389 A1 | 12/2004 | Case et al. |
| 2004/0260394 A1 | 12/2004 | Douk et al. |
| 2004/0267357 A1 | 12/2004 | Allen et al. |
| 2005/0010246 A1 | 1/2005 | Streeter |
| 2005/0010285 A1 | 1/2005 | Lambrecht et al. |
| 2005/0010287 A1 | 1/2005 | Macoviak |
| 2005/0015112 A1 | 1/2005 | Cohn et al. |
| 2005/0027348 A1 | 2/2005 | Case et al. |
| 2005/0033398 A1 | 2/2005 | Seguin |
| 2005/0043790 A1 | 2/2005 | Seguin |
| 2005/0049692 A1 | 3/2005 | Numamoto |
| 2005/0049696 A1 | 3/2005 | Siess |
| 2005/0055088 A1 | 3/2005 | Liddicoat et al. |
| 2005/0060029 A1 | 3/2005 | Le |
| 2005/0060030 A1 | 3/2005 | Lashinski et al. |
| 2005/0075584 A1 | 4/2005 | Cali |
| 2005/0075712 A1 | 4/2005 | Biancucci |
| 2005/0075717 A1 | 4/2005 | Nguyen |
| 2005/0075719 A1 | 4/2005 | Bergheim |
| 2005/0075724 A1 | 4/2005 | Svanidze |
| 2005/0075727 A1 | 4/2005 | Wheatley |
| 2005/0075730 A1 | 4/2005 | Myers |
| 2005/0075731 A1 | 4/2005 | Artof |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0107871 A1 | 5/2005 | Realyvasquez et al. |
| 2005/0113910 A1 | 5/2005 | Paniagua |
| 2005/0119688 A1 | 6/2005 | Bergheim |
| 2005/0131438 A1 | 6/2005 | Cohn |
| 2005/0137686 A1 | 6/2005 | Salahieh |
| 2005/0137688 A1 | 6/2005 | Salahieh et al. |
| 2005/0137692 A1 | 6/2005 | Haug |
| 2005/0137695 A1 | 6/2005 | Salahieh |
| 2005/0137701 A1 | 6/2005 | Salahieh |
| 2005/0143807 A1 | 6/2005 | Pavcnik et al. |
| 2005/0143809 A1 | 6/2005 | Salahieh |
| 2005/0148997 A1 | 7/2005 | Valley et al. |
| 2005/0149181 A1 | 7/2005 | Eberhardt |
| 2005/0165477 A1 | 7/2005 | Anduiza et al. |
| 2005/0187616 A1 | 8/2005 | Realyvasquez |
| 2005/0197695 A1 | 9/2005 | Stacchino et al. |
| 2005/0203549 A1 | 9/2005 | Realyvasquez |
| 2005/0203605 A1 | 9/2005 | Dolan |
| 2005/0203618 A1 | 9/2005 | Sharkawy |
| 2005/0222674 A1 | 10/2005 | Paine |
| 2005/0228495 A1 | 10/2005 | Macoviak |
| 2005/0234546 A1 | 10/2005 | Nugent |
| 2005/0240200 A1 | 10/2005 | Bergheim |
| 2005/0240263 A1 | 10/2005 | Fogarty et al. |
| 2005/0261759 A1 | 11/2005 | Lambrecht et al. |
| 2005/0283962 A1 | 12/2005 | Boudjemline |
| 2006/0004439 A1 | 1/2006 | Spenser et al. |
| 2006/0004469 A1 | 1/2006 | Sokel |
| 2006/0009841 A1 | 1/2006 | McGuckin et al. |
| 2006/0052867 A1 | 3/2006 | Revuelta et al. |
| 2006/0058775 A1 | 3/2006 | Stevens et al. |
| 2006/0089711 A1 | 4/2006 | Dolan |
| 2006/0100685 A1 | 5/2006 | Seguin et al. |
| 2006/0116757 A1 | 6/2006 | Lashinski et al. |
| 2006/0135964 A1 | 6/2006 | Vesely |
| 2006/0142848 A1 | 6/2006 | Gabbay |
| 2006/0167474 A1 | 7/2006 | Bloom et al. |
| 2006/0178740 A1 | 8/2006 | Stacchino et al. |

| | | |
|---|---|---|
| 2006/0195134 A1 | 8/2006 | Crittenden |
| 2006/0206192 A1 | 9/2006 | Tower et al. |
| 2006/0206202 A1 | 9/2006 | Bonhoeffer et al. |
| 2006/0212111 A1 | 9/2006 | Case et al. |
| 2006/0247763 A1 | 11/2006 | Slater |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0271166 A1 | 11/2006 | Thill et al. |
| 2006/0271175 A1 | 11/2006 | Woolfson et al. |
| 2006/0276874 A1 | 12/2006 | Wilson et al. |
| 2006/0276882 A1 | 12/2006 | Case et al. |
| 2006/0282161 A1 | 12/2006 | Huynh et al. |
| 2007/0005129 A1 | 1/2007 | Damm et al. |
| 2007/0005131 A1 | 1/2007 | Taylor |
| 2007/0010878 A1 | 1/2007 | Raffiee et al. |
| 2007/0016286 A1 | 1/2007 | Case et al. |
| 2007/0027518 A1 | 2/2007 | Herrmann et al. |
| 2007/0027533 A1 | 2/2007 | Douk |
| 2007/0038295 A1 | 2/2007 | Case et al. |
| 2007/0043431 A1 | 2/2007 | Melsheimer |
| 2007/0043435 A1 * | 2/2007 | Seguin et al. ................ 623/2.11 |
| 2007/0051377 A1 | 3/2007 | Douk et al. |
| 2007/0073392 A1 | 3/2007 | Heyninck-Janitz |
| 2007/0078509 A1 | 4/2007 | Lotfy et al. |
| 2007/0078510 A1 * | 4/2007 | Ryan ........................... 623/1.26 |
| 2007/0088431 A1 | 4/2007 | Bourang et al. |
| 2007/0093869 A1 | 4/2007 | Bloom et al. |
| 2007/0100439 A1 | 5/2007 | Cangialosi |
| 2007/0100440 A1 | 5/2007 | Figulla |
| 2007/0100449 A1 | 5/2007 | O'Neil et al. |
| 2007/0112415 A1 | 5/2007 | Bartlett |
| 2007/0112422 A1 | 5/2007 | Dehdashtian |
| 2007/0142907 A1 * | 6/2007 | Moaddeb et al. ............ 623/2.11 |
| 2007/0162102 A1 | 7/2007 | Ryan et al. |
| 2007/0162113 A1 | 7/2007 | Sharkawy et al. |
| 2007/0185513 A1 | 8/2007 | Woolfson et al. |
| 2007/0203391 A1 | 8/2007 | Bloom et al. |
| 2007/0213813 A1 * | 9/2007 | Von Segesser et al. ...... 623/2.18 |
| 2007/0225681 A1 | 9/2007 | House |
| 2007/0232898 A1 | 10/2007 | Huynh et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0238979 A1 | 10/2007 | Huynh et al. |
| 2007/0239254 A1 | 10/2007 | Marchand et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239271 A1 | 10/2007 | Nguyen |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255394 A1 | 11/2007 | Ryan |
| 2007/0255396 A1 | 11/2007 | Douk et al. |
| 2007/0288000 A1 | 12/2007 | Bonan |
| 2007/0288087 A1 * | 12/2007 | Fearnot et al. ................ 623/1.24 |
| 2008/0004696 A1 | 1/2008 | Vesely |
| 2008/0009940 A1 | 1/2008 | Cribier |
| 2008/0015671 A1 | 1/2008 | Bonhoeffer |
| 2008/0021552 A1 | 1/2008 | Gabbay |
| 2008/0048656 A1 | 2/2008 | Tan |
| 2008/0065001 A1 | 3/2008 | Marchand et al. |
| 2008/0065206 A1 | 3/2008 | Liddicoat |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0077234 A1 | 3/2008 | Styrc |
| 2008/0082165 A1 | 4/2008 | Wilson et al. |
| 2008/0082166 A1 | 4/2008 | Styrc et al. |
| 2008/0133003 A1 | 6/2008 | Seguin et al. |
| 2008/0140189 A1 | 6/2008 | Nguyen et al. |
| 2008/0147105 A1 | 6/2008 | Wilson et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0154355 A1 | 6/2008 | Benichou et al. |
| 2008/0154356 A1 | 6/2008 | Obermiller et al. |
| 2008/0161910 A1 | 7/2008 | Revuelta et al. |
| 2008/0161911 A1 | 7/2008 | Revuelta et al. |
| 2008/0183273 A1 | 7/2008 | Mesana et al. |
| 2008/0188928 A1 | 8/2008 | Salahieh et al. |
| 2008/0215143 A1 | 9/2008 | Seguin et al. |
| 2008/0215144 A1 | 9/2008 | Ryan et al. |
| 2008/0228254 A1 | 9/2008 | Ryan |
| 2008/0228263 A1 | 9/2008 | Ryan |
| 2008/0234797 A1 | 9/2008 | Styrc |
| 2008/0243246 A1 | 10/2008 | Ryan et al. |
| 2008/0255651 A1 | 10/2008 | Dwork |
| 2008/0255660 A1 | 10/2008 | Guyenot et al. |
| 2008/0255661 A1 | 10/2008 | Straubinger et al. |
| 2008/0262593 A1 | 10/2008 | Ryan et al. |
| 2008/0269878 A1 | 10/2008 | Iobbi |
| 2009/0005863 A1 * | 1/2009 | Goetz et al. ................... 623/2.18 |
| 2009/0012600 A1 | 1/2009 | Styrc et al. |
| 2009/0048656 A1 | 2/2009 | Wen |
| 2009/0054976 A1 | 2/2009 | Tuval et al. |
| 2009/0062907 A1 * | 3/2009 | Quijano et al. ............... 623/1.24 |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0082858 A1 | 3/2009 | Nugent et al. |
| 2009/0085900 A1 | 4/2009 | Weiner |
| 2009/0099653 A1 | 4/2009 | Suri et al. |
| 2009/0138079 A1 | 5/2009 | Tuval et al. |
| 2009/0164004 A1 | 6/2009 | Cohn |
| 2009/0164006 A1 | 6/2009 | Seguin et al. |
| 2009/0171447 A1 | 7/2009 | VonSegesser et al. |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0198315 A1 * | 8/2009 | Boudjemline .................. 623/1.2 |
| 2009/0198316 A1 | 8/2009 | Laske et al. |
| 2009/0216310 A1 | 8/2009 | Straubinger et al. |
| 2009/0216312 A1 | 8/2009 | Straubinger et al. |
| 2009/0216313 A1 | 8/2009 | Straubinger et al. |
| 2009/0222082 A1 | 9/2009 | Lock et al. |
| 2009/0234443 A1 | 9/2009 | Ottma et al. |
| 2009/0240264 A1 | 9/2009 | Tuval et al. |
| 2009/0240320 A1 | 9/2009 | Tuval |
| 2009/0287296 A1 | 11/2009 | Manasse |
| 2010/0004740 A1 | 1/2010 | Seguin et al. |
| 2010/0030328 A1 | 2/2010 | Seguin et al. |
| 2010/0036479 A1 | 2/2010 | Hill et al. |
| 2010/0036485 A1 | 2/2010 | Seguin |
| 2010/0069852 A1 | 3/2010 | Kelley |
| 2010/0094411 A1 | 4/2010 | Tuval et al. |
| 2010/0100167 A1 | 4/2010 | Bortlein et al. |
| 2010/0131054 A1 | 5/2010 | Tuval et al. |
| 2010/0137979 A1 | 6/2010 | Tuval et al. |
| 2010/0145439 A1 | 6/2010 | Seguin et al. |
| 2010/0152840 A1 | 6/2010 | Seguin et al. |
| 2010/0161045 A1 | 6/2010 | Righini |
| 2010/0198346 A1 | 8/2010 | Keogh et al. |
| 2010/0234940 A1 | 9/2010 | Dolan |
| 2010/0256723 A1 | 10/2010 | Murray |

FOREIGN PATENT DOCUMENTS

| | | |
|---|---|---|
| DE | 3640745 | 6/1987 |
| DE | 195 32 846 | 3/1997 |
| DE | 195 46 692 A1 | 6/1997 |
| DE | 195 46 692 C2 | 6/1997 |
| DE | 198 57 887 A1 | 7/2000 |
| DE | 199 07 646 | 8/2000 |
| DE | 100 10 074 | 10/2001 |
| DE | 100 49 812 | 4/2002 |
| DE | 100 49 813 | 4/2002 |
| DE | 100 49 815 | 4/2002 |

| | | |
|---|---|---|
| EP | 1057460 A1 | 6/2000 |
| EP | 1255510 | 11/2002 |
| EP | 1469797 | 11/2005 |
| FR | 2788217 | 12/1999 |
| FR | 2815844 | 5/2000 |
| GB | 2056023 | 3/1981 |
| GB | 2433700 | 12/2007 |
| SU | 1271508 | 11/1986 |
| WO | 95/29640 | 11/1995 |
| WO | 00/44313 | 8/2000 |
| WO | 00/47136 | 8/2000 |
| WO | 01/35870 | 5/2001 |
| WO | 01/49213 | 7/2001 |
| WO | 01/54625 | 8/2001 |
| WO | 01/62189 | 8/2001 |
| WO | 01/64137 | 9/2001 |
| WO | 02/22054 | 3/2002 |
| WO | 02/36048 | 5/2002 |
| WO | 03/003943 | 1/2003 |
| WO | 03/003949 | 1/2003 |
| WO | 03/011195 | 2/2003 |
| WO | 2004/019825 | 3/2004 |
| WO | 2004/089250 | 10/2004 |
| WO | 2005/004753 | 1/2005 |
| WO | 2005/046528 | 5/2005 |
| WO | 2006/026371 | 3/2006 |
| WO | 2008/047354 | 4/2008 |
| WO | 2008/138584 | 11/2008 |
| WO | 2008/150529 | 12/2008 |
| WO | 2009/002548 | 12/2008 |
| WO | 2009/029199 | 3/2009 |
| WO | 2009/042196 | 4/2009 |
| WO | 2009/045338 | 4/2009 |
| WO | 2009/061389 | 5/2009 |
| WO | 2009/091509 | 7/2009 |
| WO | 2009/111241 | 9/2009 |

OTHER PUBLICATIONS

Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.
Bailey, "Percutaneous Expandable Prosthetic Valves," In: Topol EJ, ed. Textbook of Interventional Cardiology. vol. 11. Second edition. WB Saunders, Philadelphia, 1994:1268-1276.
Block, et al., "Percutaneous Approaches to Valvular Heart Disease," Current Cardiology Reports, vol. 7 (2005) pp. 108-113.
Bonhoeffer, et al, "Percutaneous Insertion of the Pulmonary Valve," Journal of the American College of Cardiology (United States), May 15, 2002, pp. 1664-1669.
Bonhoeffer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.
Bonhoeffer, et al, "Transcatheter Implantation of a Bovine Valve in Pulmonary Position: A Lamb Study," Circulation (United States), Aug. 15, 2000, pp. 813-816.
Boudjemline, et al, "Images in Cardiovascular Medicine. Percutaneous Aortic Valve Replacement in Animals," Circulation (United States), Mar. 16, 2004, 109, p. e161.
Boudjemline, et al. "Is Percutaneous Implantation of a Bovine Venous Valve in the Inferior Vena Cava a Reliable Technique to Treat Chronic Venous Insufficiency Syndrome?" Medical Science Monitor—International Medical Journal of Experimental and Clinical Research (Poland), Mar. 2004, pp. BR61-BR66.
Boudjemline, et al, "Off-pump Replacement of the Pulmonary Valve in Large Right Ventricular Outflow Tracts: A Hybrid Approach," Journal of Thoracic and Cardiovascular Surgery (United States), Apr. 2005, pp. 831-837.
Boudjemline, et al, "Percutaneous Aortic Valve Replacement: Will We Get There?" Heart (British Cardiac Society) (England), Dec. 2001, pp. 705-706.
Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-BR116.

Boudjemline, et al, "Percutaneous Implantation of a Biological Valve in Aortic Position: Preliminary Results in a Sheep Study," European Heart Journal 22, Sep. 2001, p. 630.
Boudjemline, et al, "Percutaneous Implantation of a Valve in the Descending Aorta in Lambs," European Heart Journal (England), Jul. 2002, pp. 1045-1049.
Boudjemline, et al, "Percutaneous Pulmonary Valve Replacement in a Large Right Ventricular Outflow Tract: An Experimental Study," Journal of the American College of Cardiology (United States), Mar. 17, 2004, pp. 1082-1087.
Boudjemline, et al, "Percutaneous Valve Insertion: A New Approach," Journal of Thoracic and Cardiovascular Surgery (United States), Mar. 2003, pp. 741-742.
Boudjemline, et al, "Stent Implantation Combined with a Valve Replacement to Treat Degenerated Right Ventricle to Pulmonary Artery Prosthetic Conduits," European Heart Journal 22, Sep. 2001, p. 355.
Boudjemline, et al, "Steps Toward Percutaneous Aortic Valve Replacement," Circulation (United States), Feb. 12, 2002, pp. 775-778.
Boudjemline, et al, "The Percutaneous Implantable Heart Valve," Progress in Pediatric Cardiology (Ireland), 2001, pp. 89-93.
Boudjemline, et al, "Transcatheter Reconstruction of the Right Heart," Cardiology in the Young (England), Jun. 2003, pp. 308-311.
Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.
Cribier, A. et al, "Percutaneous Transcatheter Implantation of an Aortic Valve Prosthesis for Calcific Aortic Stenosis: First Human Case Description," Circulation (2002) 3006-3008.
Davidson et al., "Percutaneous therapies for valvular heart disease," Cardiovascular Pathology 15 (2006) 123-129.
Hanzel, et al., "Complications of percutaneous aortic valve replacement: experience with the Criber-Edwards™ percutaneous heart valve," EuroIntervention Supplements (2006), I (Supplement A) A3-A8.
Huber, et al., "Do Valved Stents Compromise Coronary Flow?" Eur. J. Cardiothorac. Surg. 2004;25:754-759.
Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.
Khambadkone, et al, "Percutaneous Implantation of Pulmonary Valves," Expert Review of Cardiovascular Therapy (England), Nov. 2003, pp. 541-548.
Khambadkone, et al, "Percutaneous Pulmonary Valve Implantation: Early and Medium Term Results," Circulation 108 (17 Supplement), Oct. 28, 2003, p. IV-375.
Khambadkone, et al. "Percutaneous Pulmonary Valve Implantation: Impact of Morphology on Case Selection," Circulation 108 (17 Supplement), Oct. 28, 2003, p. IV-642-IV-643.
Lutter, et al, "Percutaneous Aortic Valve Replacement: An Experimental Study. I. Studies on Implantation," The Journal of Thoracic and Cardiovascular Surgery, Apr. 2002, pp. 768-776.
Lutter, et al, "Percutaneous Valve Replacement: Current State and Future Prospects," Annals of Thoracic Surgery (Netherlands), Dec. 2004, pp. 2199-2206.
Ma, Ling., et al., "Double-crowned valved stents for off-pump mitral valve replacement," European Journal of Cardio Thoracic Surgery, 28:194-198, 2005.
Medtech Insight, "New Frontiers in Heart Valve Disease," vol. 7, No. 8 (2005).
Palacios, "Percutaneous Valve Replacement and Repair, Fiction or Reality?" Journal of American College of Cardiology, vol. 44, No. 8 (2004) pp. 1662-1663.
Pelton et al., "Medical Uses of Nitinol," Materials Science Forum vols. 327-328, pp. 63-70 (2000).
Ruiz, "Transcathether Aortic Valve Implantation and Mitral Valve Repair: State of the Art," Pediatric Cardiology, vol. 26, No. 3 (2005).
Saliba, et al, "Treatment of Obstructions of Prosthetic Conduits by Percutaneous Implantation of Stents," Archives des Maldies du Coeur et des Vaisseaux (France), 1999, pp. 591-596.

Webb, et al., "Percutaneous Aortic Valve Implantation Retrograde from the Femoral Artery," Circulation (2006), 113;842-850.

Stassano et al., "Mid-term results of the valve-on-valve technique for bioprosthetic failure," Eur. J. Cardiothorac. Surg. 2000; 18:453-457.

Pavcnik et al., "Aortic and venous valve for percutaneous insertion," Min. Invas. Ther. & Allied Techol. 2000, vol. 9, pp. 287-292.

* cited by examiner

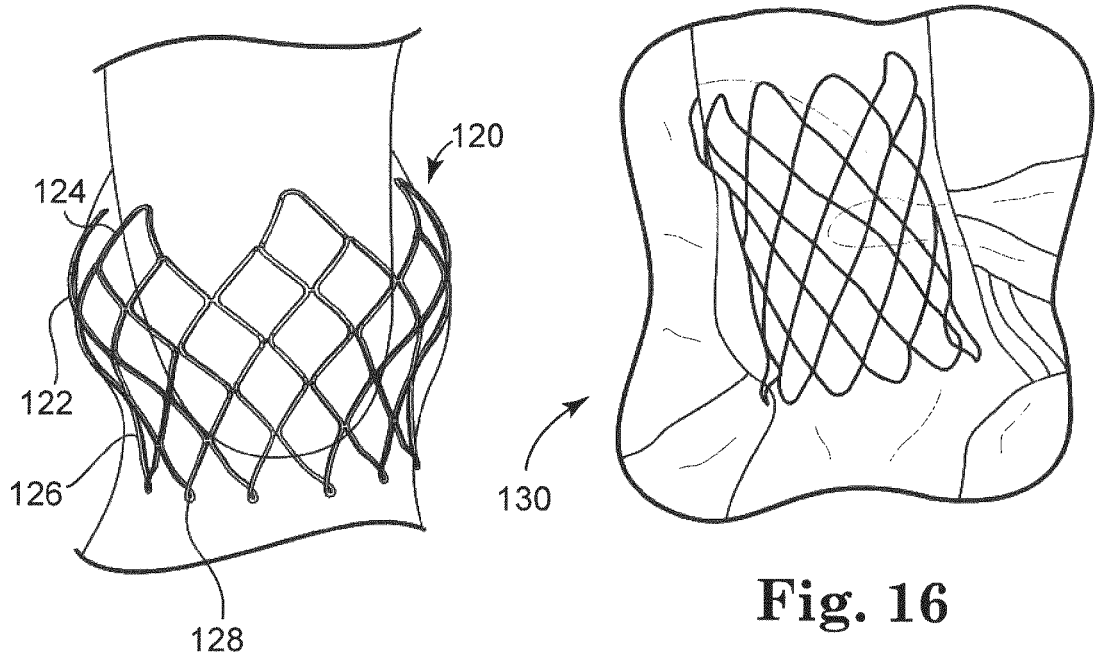
Fig. 15
Fig. 16
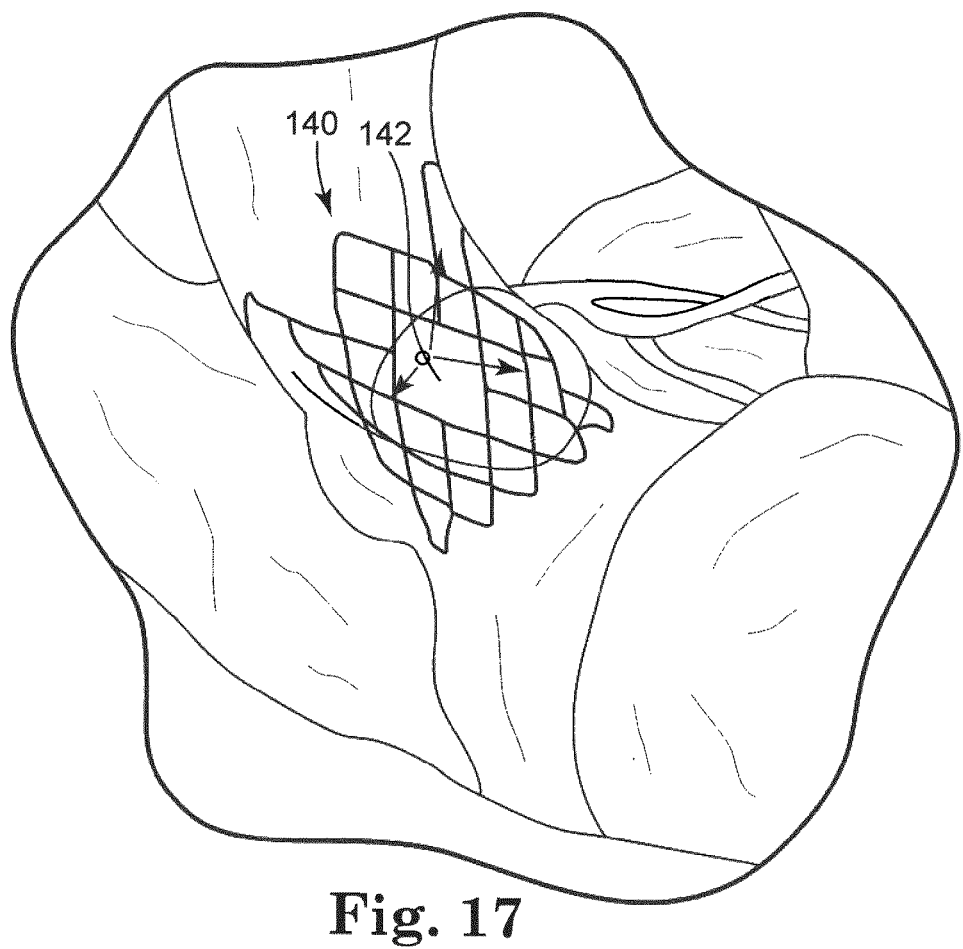
Fig. 17

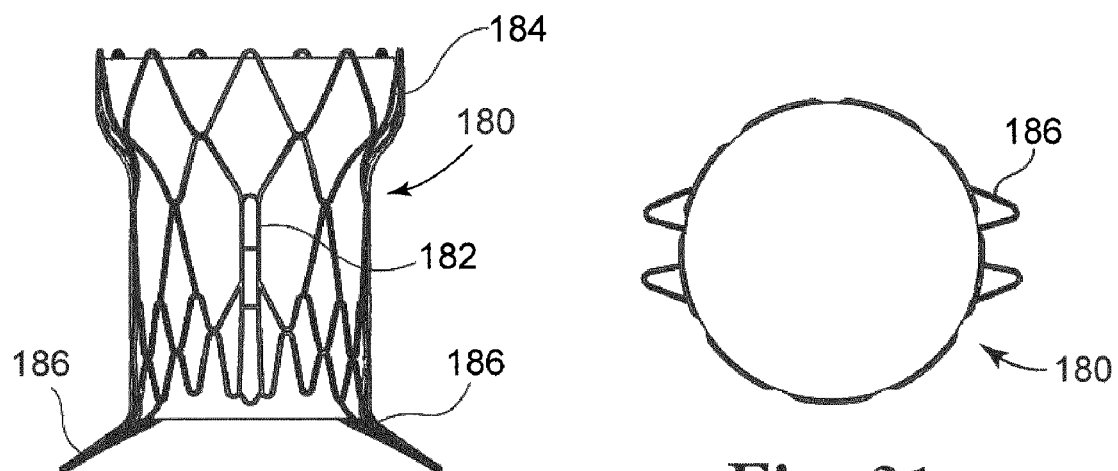
Fig. 20
Fig. 21
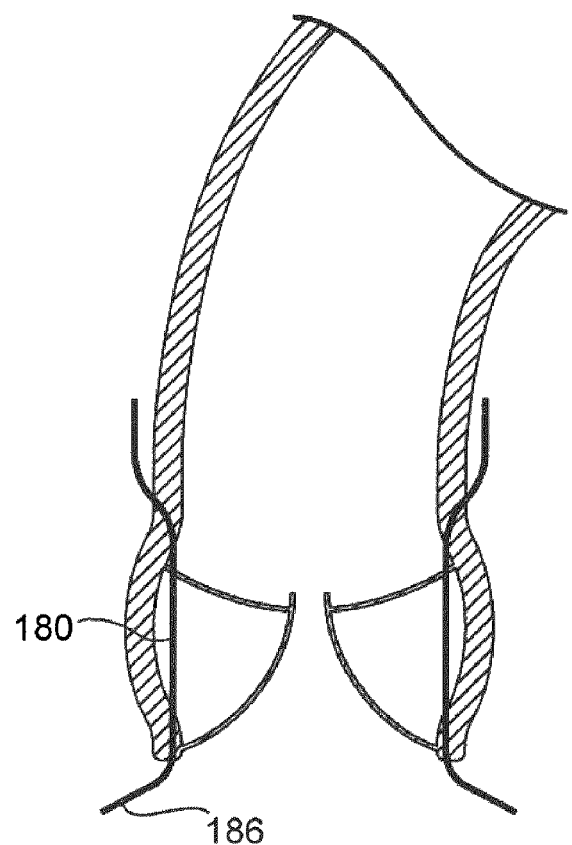
Fig. 22

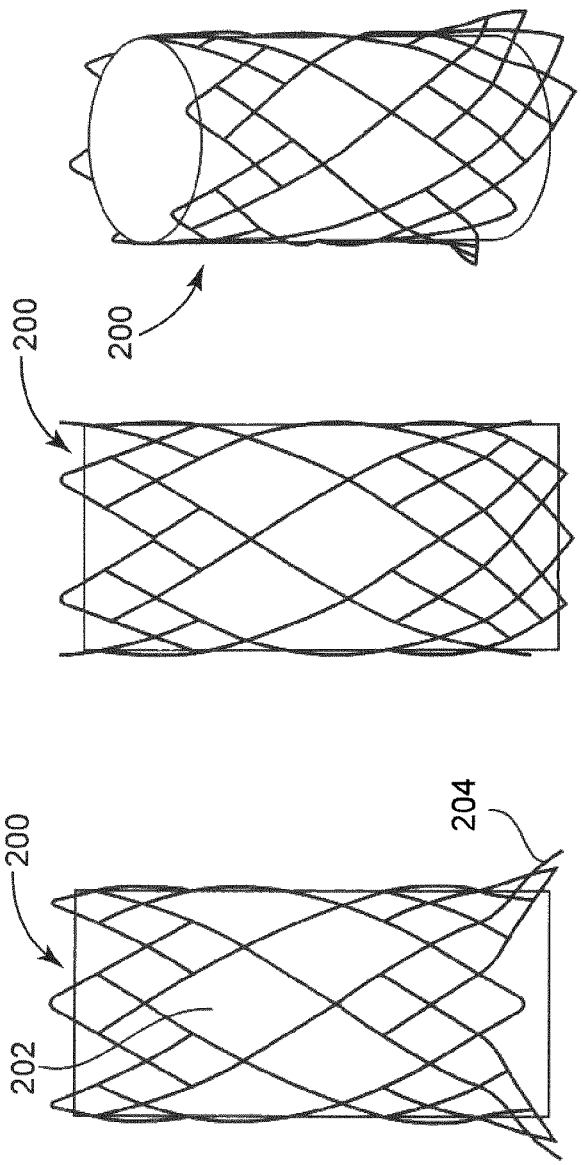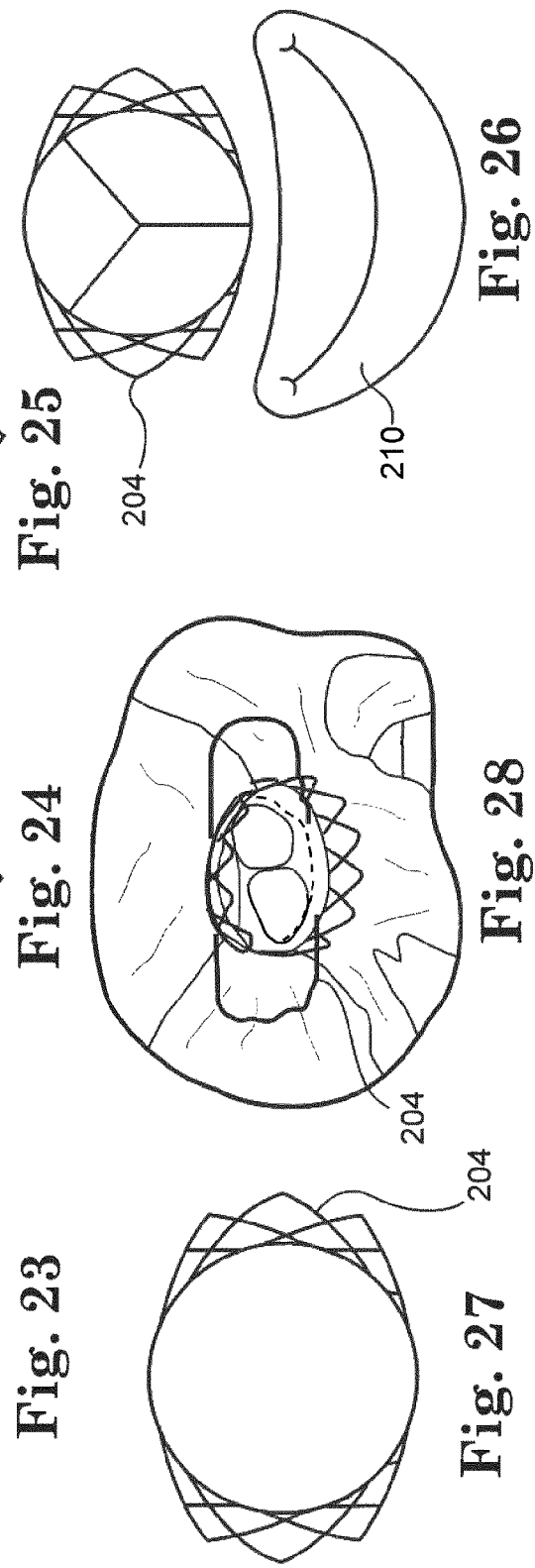

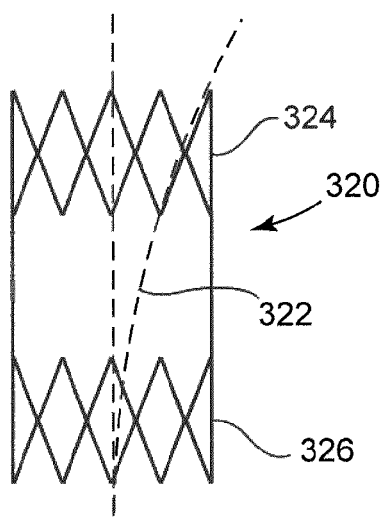
Fig. 46
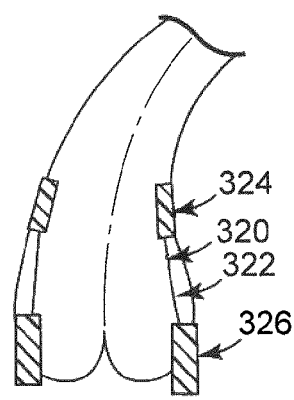
Fig. 47
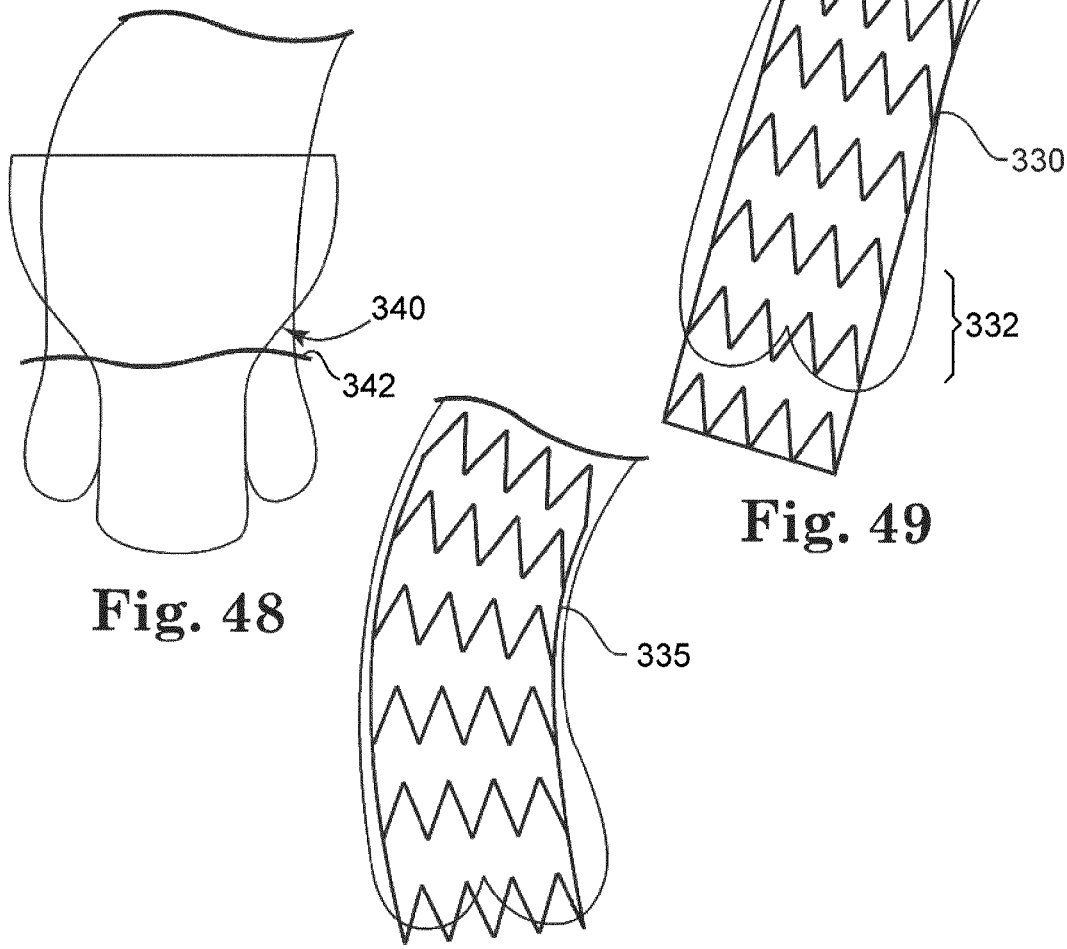
Fig. 48
Fig. 49
Fig. 50

STENTS FOR PROSTHETIC HEART VALVES

CROSS-REFERENCE TO RELATED APPLICATION

The present application claims priority to U.S. Provisional Application Nos. 61/062,207, filed Jan. 24, 2008, and titled "Delivery Systems and Methods of Implantation for Prosthetic Heart Valves"; and 61/075,902, filed Jun. 26, 2008 and titled "Heart Valve"; the entire contents of which are incorporated herein by reference in their entireties.

TECHNICAL FIELD

The present invention relates to prosthetic heart valves. More particularly, it relates to devices, methods, and delivery systems for percutaneously implanting prosthetic heart valves.

BACKGROUND

Diseased or otherwise deficient heart valves can be repaired or replaced using a variety of different types of heart valve surgeries. Typical heart valve surgeries involve an open-heart surgical procedure that is conducted under general anesthesia, during which the heart is stopped while blood flow is controlled by a heart-lung bypass machine. This type of valve surgery is highly invasive and exposes the patient to a number of potentially serious risks, such as infection, stroke, renal failure, and adverse effects associated with use of the heart-lung machine, for example.

Recently, there has been increasing interest in minimally invasive and percutaneous replacement of cardiac valves. Such surgical techniques involve making a very small opening in the skin of the patient into which a valve assembly is inserted in the body and delivered to the heart via a delivery device similar to a catheter. This technique is often preferable to more invasive forms of surgery, such as the open-heart surgical procedure described above. In the context of pulmonary valve replacement, U.S. Patent Application Publication Nos. 2003/0199971 A1 and 2003/0199963 A1, both filed by Tower, et al., describe a valved segment of bovine jugular vein, mounted within an expandable stent, for use as a replacement pulmonary valve. The replacement valve is mounted on a balloon catheter and delivered percutaneously via the vascular system to the location of the failed pulmonary valve and expanded by the balloon to compress the valve leaflets against the right ventricular outflow tract, anchoring and sealing the replacement valve. As described in the articles: "Percutaneous Insertion of the Pulmonary Valve", Bonhoeffer, et al., Journal of the American College of Cardiology 2002; 39: 1664-1669 and "Transcatheter Replacement of a Bovine Valve in Pulmonary Position", Bonhoeffer, et al., Circulation 2000; 102: 813-816, the replacement pulmonary valve may be implanted to replace native pulmonary valves or prosthetic pulmonary valves located in valved conduits.

Various types and configurations of prosthetic heart valves are used in percutaneous valve procedures to replace diseased natural human heart valves. The actual shape and configuration of any particular prosthetic heart valve is dependent to some extent upon the valve being replaced (i.e., mitral valve, tricuspid valve, aortic valve, or pulmonary valve). In general, the prosthetic heart valve designs attempt to replicate the function of the valve being replaced and thus will include valve leaflet-like structures used with either bioprostheses or mechanical heart valve prostheses. In other words, the replacement valves may include a valved vein segment that is mounted in some manner within an expandable stent to make a stented valve. In order to prepare such a valve for percutaneous implantation, the stented valve can be initially provided in an expanded or uncrimped condition, then crimped or compressed around the balloon portion of a catheter until it is as close to the diameter of the catheter as possible.

Other percutaneously-delivered prosthetic heart valves have been suggested having a generally similar configuration, such as by Bonhoeffer, P. et al., "Transcatheter Implantation of a Bovine Valve in Pulmonary Position." Circulation, 2002; 102:813-816, and by Cribier, A. et al. "Percutaneous Transcatheter Implantation of an Aortic Valve Prosthesis for Calcific Aortic Stenosis." Circulation, 2002; 106:3006-3008, the disclosures of which are incorporated herein by reference. These techniques rely at least partially upon a frictional type of engagement between the expanded support structure and the native tissue to maintain a position of the delivered prosthesis, although the stents can also become at least partially embedded in the surrounding tissue in response to the radial force provided by the stent and balloons used to expand the stent. Thus, with these transcatheter techniques, conventional sewing of the prosthetic heart valve to the patient's native tissue is not necessary. Similarly, in an article by Bonhoeffer, P. et al. titled "Percutaneous Insertion of the Pulmonary Valve." J Am Coll Cardiol, 2002; 39:1664-1669, the disclosure of which is incorporated herein by reference, percutaneous delivery of a biological valve is described. The valve is sutured to an expandable stent within a previously implanted valved or non-valved conduit, or a previously implanted valve. Again, radial expansion of the secondary valve stent is used for placing and maintaining the replacement valve.

Although there have been advances in percutaneous valve replacement techniques and devices, there is a continued desire to provide different designs of cardiac valves that can be implanted in a minimally invasive and percutaneous manner. It is additionally desirable to provide valves that are resistant to migration after they are implanted.

SUMMARY

The replacement heart valves of the invention each include a stent to which a valve structure is attached. The stents of the invention include a wide variety of structures and features that can be used alone or in combination with features of other stents of the invention. Many of the structures are compressible to a relatively small diameter for percutaneous delivery to the heart of the patient, and then are expandable either via removal of external compressive forces (e.g., self-expanding stents), or through application of an outward radial force (e.g., balloon expandable stents). The devices delivered by the delivery systems described herein can be used to deliver stents, valved stents, or other interventional devices such as ASD (atrial septal defect) closure devices, VSD (ventricular septal defect) closure devices, or PFO (patent foramen ovale) occluders.

Methods for insertion of the replacement heart valves of the invention include delivery systems that can maintain the stent structures in their compressed state during their insertion and allow or cause the stent structures to expand once they are in their desired location. In addition, delivery methods of the invention can include features that allow the stents to be retrieved for removal or relocation thereof after they have been deployed or partially deployed from the stent delivery systems. The methods may include implantation of the stent structures using either an antegrade or retrograde approach. Further, in many of the delivery approaches of the invention, the stent structure is rotatable in vivo to allow the stent structure to be positioned in a desired orientation.

The stent structures of the invention can provide resistance to leaflet abrasion via the configuration of the wires or other structural elements relative to each other. Other stent structures can provide for reduced crown density and various other configurations of wire shapes and features for use with attached valves for valve replacement procedures.

BRIEF DESCRIPTION OF THE DRAWINGS

The present invention will be further explained with reference to the appended Figures, wherein like structure is referred to by like numerals throughout the several views, and wherein:

FIGS. 15-18 are perspective views of different stent embodiments, each positioned within a heart vessel;

FIG. 20 is a front view of a stent embodiment;

FIG. 21 is a top view of the stent of FIG. 20;

FIG. 22 is a schematic front view of the stent of FIG. 20 positioned in a heart vessel;

FIG. 23 is a front view of another stent embodiment;

FIG. 24 is a side view of the stent of FIG. 23;

FIG. 25 is a perspective view of the stent of FIG. 23, positioned on a mandrel;

FIG. 26 is a top view of the stent of FIG. 23 positioned relative to a schematic view of a heart vessel, wherein the stent includes leaflets in its interior portion;

FIG. 27 is a top view of the stent of FIG. 23;

FIG. 28 is a perspective top view of the stent of FIG. 23 positioned in a heart;

FIG. 46 is a front view of another stent embodiment;

FIGS. 47-50 are front schematic views of embodiments of stents positioned in a heart vessel;

DETAILED DESCRIPTION

Figure 1:
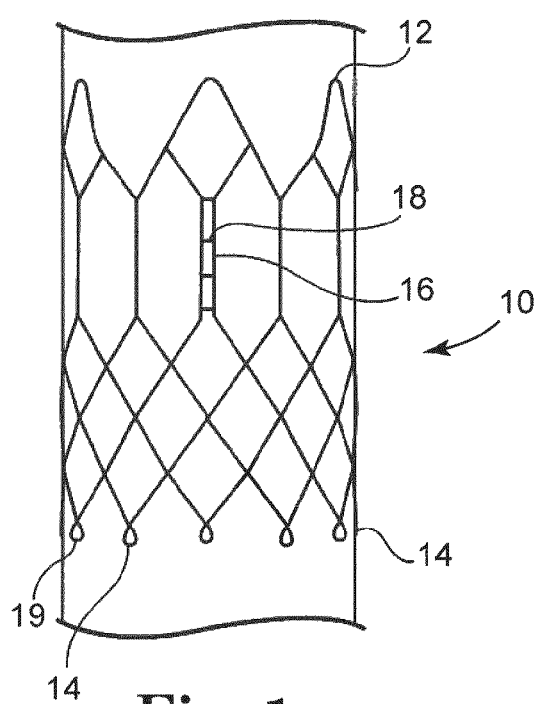
FIG. 1 is a front view of an embodiment of a stent in accordance with the invention.

As referred to herein, the prosthetic heart valves used in accordance with various devices and methods of heart valve delivery may include a wide variety of different configurations, such as a prosthetic heart valve having tissue leaflets or a synthetic heart valve having polymeric, metallic, or tissue-engineered leaflets, and can be specifically configured for replacing any heart valve. That is, while much of the description herein refers to replacement of aortic valves, the prosthetic heart valves of the invention can also generally be used for replacement of native mitral, pulmonic, or tricuspid valves, for use as a venous valve, or to replace a failed bioprosthesis, such as in the area of an aortic valve or mitral valve, for example.

Although each of the valves used with the delivery devices and methods described herein would typically include leaflets attached within an interior area of a stent, the leaflets are not shown in many of the illustrated embodiments for clarity purposes. In general, the stents described herein include a support structure comprising a number of strut or wire portions arranged relative to each other to provide a desired compressibility, strength, and leaflet attachment zone(s) to the heart valve. Other details on particular configurations of the stents of the invention are also described below; however, in general terms, stents of the invention are generally tubular support structures, and leaflets will be secured to the support structure to provide a valved stent. The leaflets can be formed from a variety of materials, such as autologous tissue, xenograph material, or synthetics as are known in the art. The leaflets may be provided as a homogenous, biological valve structure, such as a porcine, bovine, or equine valve. Alternatively, the leaflets can be provided independent of one another (e.g., bovine or equine pericardial leaflets) and subsequently assembled to the support structure of the stent. In another alternative, the stent and leaflets can be fabricated at the same time, such as may be accomplished using high strength nano-manufactured NiTi films of the type produced at Advanced Bio Prosthetic Surfaces Ltd. (ABPS) of San Antonio, Tex., for example. The support structures are generally configured to accommodate three leaflets; however, the replacement prosthetic heart valves of the invention can incorporate more or less than three leaflets.

In more general terms, the combination of a support structure with one or more leaflets can assume a variety of other configurations that differ from those shown and described, including any known prosthetic heart valve design. In certain embodiments of the invention, the support structure with leaflets utilize certain features of known expandable prosthetic heart valve configurations, whether balloon expandable, self-expanding, or unfurling (as described, for example, in U.S. Pat. Nos. 3,671,979; 4,056,854; 4,994,077; 5,332,402; 5,370,685; 5,397,351; 5,554,185; 5,855,601; and 6,168,614; U.S. Patent Application Publication No. 2004/0034411; Bonhoeffer P., et al., "Percutaneous Insertion of the Pulmonary Valve", Pediatric Cardiology, 2002; 39:1664-1669; Anderson H R, et al., "Transluminal Implantation of Artificial Heart Valves", EUR Heart J., 1992; 13:704-708; Anderson, J. R., et al., "Transluminal Catheter Implantation of New Expandable Artificial Cardiac Valve", EUR Heart J., 1990, 11: (Suppl) 224a; Hilbert S. L., "Evaluation of Explanted Polyurethane Trileaflet Cardiac Valve Prosthesis", J Thorac Cardiovascular Surgery, 1989; 94:419-29; Block P C, "Clinical and Hemodyamic Follow-Up After Percutaneous Aortic Valvuloplasty in the Elderly", The American Journal of Cardiology, Vol. 62, Oct. 1, 1998; Boudjemline, Y., "Steps Toward Percutaneous Aortic Valve Replacement", Circulation, 2002; 105:775-558; Bonhoeffer, P., "Transcatheter Implantation of a Bovine Valve in Pulmonary Position, a Lamb Study", Circulation, 2000: 102:813-816; Boudjemline, Y., "Percutaneous Implantation of a Valve in the Descending Aorta In Lambs", EUR Heart J, 2002; 23:1045-1049; Kulkinski, D., "Future Horizons in Surgical Aortic Valve Replacement: Lessons Learned During the Early Stages of Developing a Transluminal Implantation Technique", ASAIO J, 2004; 50:364-68; the teachings of which are all incorporated herein by reference).

Orientation and positioning of the stents of the invention may be accomplished either by self-orientation of the stents (such as by interference between features of the stent and a previously implanted stent or valve structure) or by manual orientation of the stent to align its features with anatomical or previous bioprosthetic features, such as can be accomplished using fluoroscopic visualization techniques, for example. For example, when aligning the stents of the invention with native anatomical structures, they should be aligned so as to not block the coronary arteries, and native mitral or tricuspid valves should be aligned relative to the anterior leaflet and/or the trigones/commissures.

Some embodiments of the support structures of the stents described herein can be a series of wires or wire segments arranged so that they are capable of transitioning from a collapsed state to an expanded state. In some embodiments, a number of individual wires comprising the support structure can be formed of a metal or other material. These wires are arranged in such a way that a support structure allows for folding or compressing to a contracted state in which its internal diameter is greatly reduced from its internal diameter in an expanded state. In its collapsed state, such a support structure with attached valves can be mounted over a delivery device, such as a balloon catheter, for example. The support structure is configured so that it can be changed to its expanded state when desired, such as by the expansion of a balloon catheter. The delivery systems used for such a stent should be provided with degrees of rotational and axial orientation capabilities in order to properly position the new stent at its desired location.

The wires of the support structure of the stents in other embodiments can alternatively be formed from a shape memory material such as a nickel titanium alloy (e.g., Nitinol) or a very high-tensile material that will expand to its original state after compression and removal of external forces. With this material, the support structure is self-expandable from a contracted state to an expanded state, such as by the application of heat, energy, and the like, or by the removal of external forces (e.g., compressive forces). This support structure can be repeatedly compressed and re-expanded without damaging the structure of the stent. In addition, the support structure of such an embodiment may be laser cut from a single piece of material or may be assembled from a number of different components. For these types of stent structures, one example of a delivery system that can be used includes a catheter with a retractable sheath that covers the stent until it is to be deployed, at which point the sheath can be retracted to allow the stent to expand. Alternatively, the stent structures of the invention can be implanted using conventional surgical techniques and/or minimally invasive surgical procedures. In such cases, the stents of the invention can advantageously require relatively few or no sutures to secure the stent to an anatomical location within the patient.

Referring now to the Figures, wherein the components are labeled with like numerals throughout the several Figures, and initially to FIGS. 1-5 illustrate stents 10, 20, 30, and 40, respectively, each of which is positioned over a mandrel. With particular reference to FIG. 1, stent 10 includes a first end 12 having six crowns and a second end 14 having twelve crowns. Each of the stent crowns at the second end 14 includes a loop or eyelet 19 that can be used for attachment to a delivery system and/or tissue valve, for example. It is contemplated that each of the crowns at the second end includes a loop or eyelet 19, as shown, or that only some of the crowns include such a loop or eyelet. The size and shape of the loops 19 can all be the same on a single stent, or they can have different sizes and/or shapes. Stent 10 further includes at least one longitudinal post 16, which can be used for attachment of tissue to the stent, along with providing additional stability to the first end 12 of the stent. The longitudinal post 16 extends generally along the annular region of the stent 10 and has a height that accommodates attachment of leaflet material. That is, the height of the post 16 is generally the same as the desired commissural height for the stent 10. As shown, the longitudinal posts 16 are comprised of two bars or vertical portions that are spaced from each other by a sufficient distance to allow leaflets to be drawn between the vertical portions at the leaflet commissures. Other skirt material portions and/or commissure protection features can also be drawn through the space between the vertical portions. The space between the vertical portions of each post 16 may have incremental steps 18, as shown in FIG. 1, which help to provide anchoring points for suturing, for example, or the posts may not include such steps, as shown with post 132 in FIG. 3, which will be discussed in further detail below. If steps 18 are provided, they can be generally perpendicular to the vertical posts, which will make the openings generally rectangular in shape, or the steps can be differently oriented and shaped so that the openings are circular, elliptical, or another chosen shape. It is further noted that the vertical portions of the posts 16 can be made of a different material or have a different thickness than the rest of the stent wires and/or the posts can be made with reinforced attachment stents or welds on the outflow end to provide additional strength in this area.

With this stent 10, wire structure extends between one end of the post 16 and the first end 12 (which may be referred to as the aortic aspect of the stent) and additional wire structure extends between the other end of the stent post and the second end 14 (which may be referred to as the ventricular aspect of the stent). The stent 10 may include one longitudinal post 16 for each commissure of the valve that will be attached thereto, if desired. That is, for a three-leaflet valve, three longitudinal posts 16 will be provided.

Figure 2:
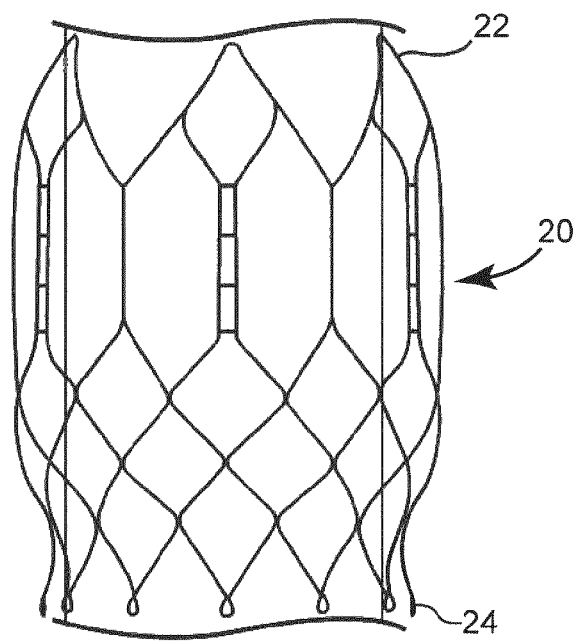
FIG. 2 is a front view of an embodiment of a stent in accordance with the invention.

The stent 20 of FIG. 2 includes multiple wires that are arranged in a generally similar configuration to that discussed above relative to FIG. 1. However, stent 20 further includes a central bulbous region between its first and second ends 22, 24 that is larger in diameter than the diameters of the first and second ends of the stent. The bulbous region can be configured to generally match the contours of the anatomy where the stent will be positioned in the patient (e.g., at the aortic valve sinus region). The first end 22 is flared inwardly (i.e., toward the central axis of the stent), preferably by an amount that is enough to be atraumatic, but not so pronounced that it loses contact with the patient's anatomy or interferes with another device (e.g., a coronary catheter) at a later date. Thus, the inward flare can be less than that shown, although it is possible that the flare is even greater than that shown. In addition, the second end 24 is slightly flared outwardly, as shown in the Figure. This flare at the second end 24 of the stent 20 (i.e., away from the central longitudinal axis of the stent) can prevent or minimize leakage between the implanted heart valve and the native annulus and/or to provide a physical and/or visual docking feature to secure the stent against a wall of a vessel or opening in the heart to prevent migration of the stent, for example. Additionally, the second end 24 can also have an at least slightly inward bend (see FIG. 3, for example) that may be advantageous when implanting this stent in the aortic region in order to minimize trauma to adjacent anatomical structures (e.g., the mitral valve anterior leaflet or the left ventricular wall). This slight inward bend can also help to minimize pressure on the septum in the area of the bundle branch, which can in turn reduce the potential for arrythmias or heart block during or after the transcatheter valve replacement procedure.

Figure 3:
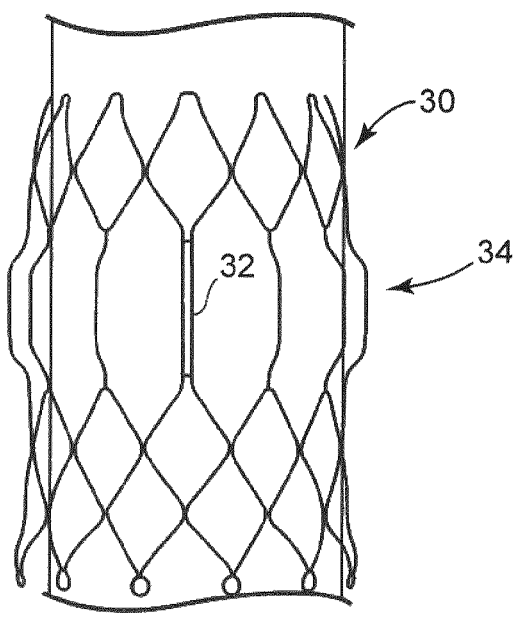
FIG. 3 is a front view of an embodiment of a stent in accordance with the invention.
Figure 4:
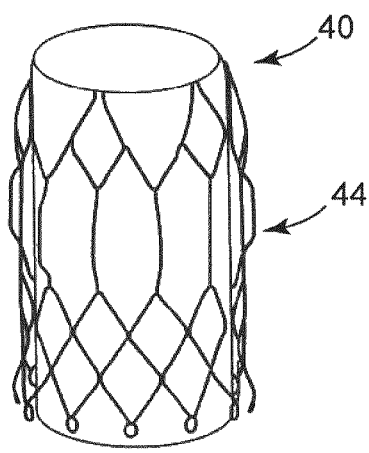
FIG. 4 is a perspective view of a stent embodiment in accordance with the invention.
Figure 5:
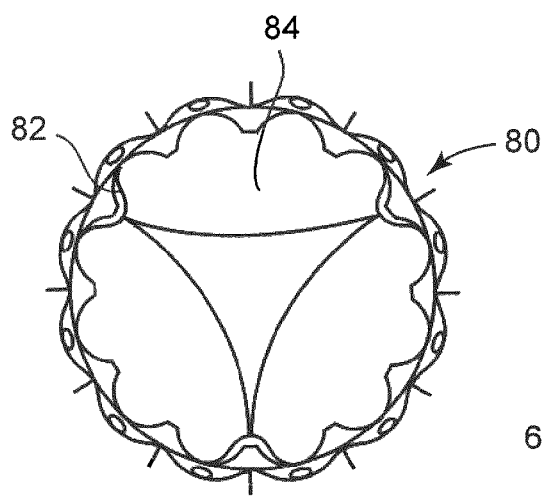
FIG. 5 is a top view of another stent embodiment.
Figure 6:
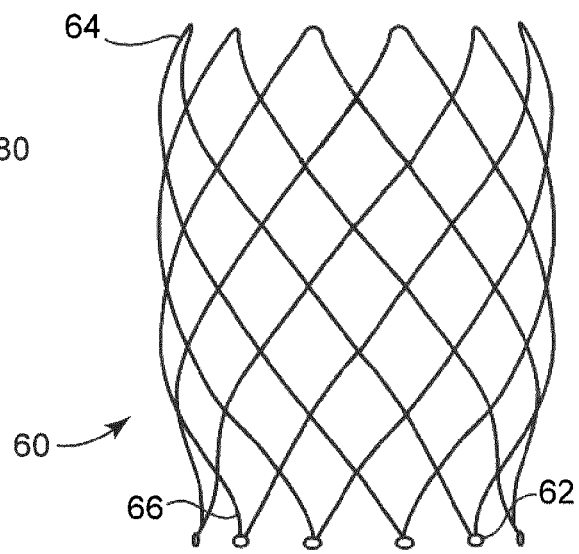
FIG. 6 is a front view of another stent embodiment.
Figure 7:
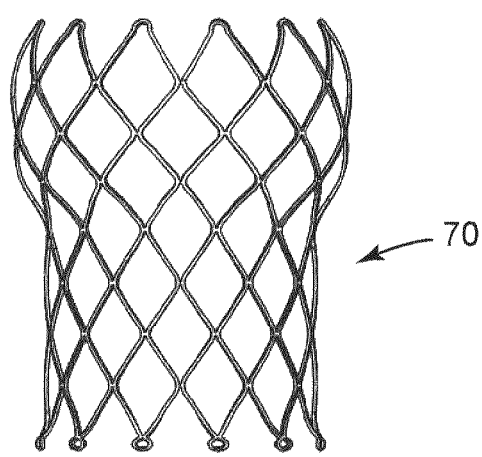
FIG. 7 is a front view of another stent embodiment.
Figure 8:
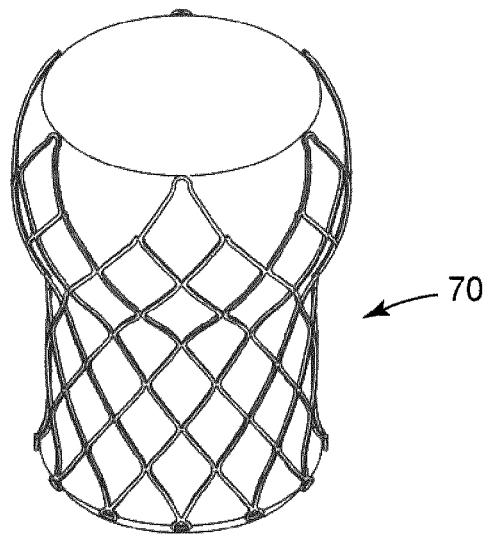
FIG. 8 is a perspective view of another stent embodiment.

FIGS. 3 and 4 illustrate stents 30 and 40 that are "selectively" flared to match particular desired shapes for portions of the stent. For example, certain stent wires are flared outwardly to avoid potential interference between the stent and the tissue leaflets of the replacement valves. The stent features to which the tissue will be attached may not be flared at all, such that the stent is relatively tubular, or these wires could instead be flared inwardly or outwardly. Stents 30, 40 include central regions 34, 44, respectively that are somewhat larger in diameter than the adjacent portions of the stent. The stent 30 further includes at least one longitudinal element or feature that can be used for attachment of tissue to the stent, such as a longitudinal post 32. Such posts 32 can also be positioned at the same distance from the longitudinal axis as the other stent elements in the central region 34, or the longitudinal posts can be closer to or further from the central axis of the stent than the other stent elements in the central region 34, if desired. By positioning the posts closer to the central axis than the other wires in the central region 34, the free edges of the dynamic leaflets positioned inside the stent 30, 40 of the new or replacement valve would be less likely to contact the stent posts when the valve leaflets are fully open. This reduced contact can reduce the potential for wear on the leaflets during valve cycling. An additional benefit of positioning the wires of the post closer to the central longitudinal axis as the other stent wires is to minimize stress at the commissures, and to help maintain coronary perfusion. This can be accomplished by limiting the opening of the leaflet so that coronary flow behind the valve leaflets is maintained. Yet another benefit of these configurations having attachment points that are inwardly offset from the largest outer diameter of the stent is that a smaller tissue valve can be used, which in turn reduces the overall transcatheter crimp profile of the delivery system.

Figure 54:
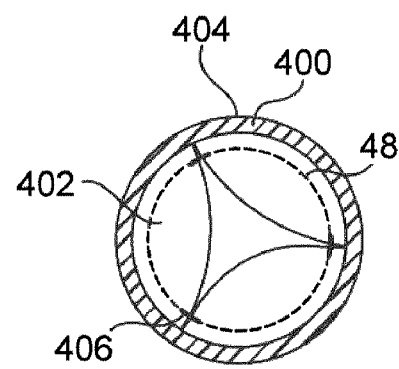
FIG. 54 is a top cross-sectional view of a valve attached within a stent frame.

Reduction of the potential wear on the valve leaflets can alternatively be accomplished by fastening leaflet commissures closer to the center of the stent than to the outer circumference. FIG. 54 illustrates such an arrangement with a schematic view of an outer stent frame 400 having three leaflets 402 arranged so that each two adjacent leaflets are attached to the stent frame 400 at a leaflet commissure area 404. Another fastening point of each of these sets of leaflets 402 at the commissure area 404 is shifted inwardly toward the center of the stent frame 400 to an inner fastening point 406. In this way, when the leaflets 402 are open, their free edges can only move out as far as the circle or inner area 408, which is shown schematically with a broken line. As shown, even if the leaflets 402 are in this fully open position, they will not contact the outer stent frame 400, thereby reducing potential wear on the valve leaflets.

Stents 10, 20, and 40 each include an arrangement of wires that provides twelve stent crowns at one end and six stent crowns at the opposite end, while stent 30 includes twelve crowns at both ends. For embodiments that include twelve crowns at the inflow end of the stent, this configuration can provide additional strength to the stent annulus area to prevent migration, to open stenotic native valve orifices, and also to provide a greater number of points for attaching pericardial leaflets to the stent. It is possible, however, to provide less than twelve (e.g., six) crowns at the outflow because the same stent strength is not required at this end for less tissue attachment points are needed. These illustrated stents are only some of the arrangements of wires that can achieve this feature of having different numbers of stent crowns at opposite ends of a single stent. In a further alternative, each of the ends of one stent can have the same number of stent crowns, but the center portion can have a more or less dense concentration of wires than either of the ends. In any case, a stent having less stent crowns at one of its ends may simplify the use of an associated delivery system, since the end with less stent crowns will have a corresponding smaller number of crowns that need to be connected to the delivery system.

FIGS. 5-8 illustrate additional stent embodiments 80, 60, 70. Stent 60 has a similar shape to the stent 20 of FIG. 2; however, stent 60 includes the same number of stent crowns at both ends, and also does not have the same longitudinal posts that are part of the wire arrangement of stent 20. Rather, stent 60 includes a generally regular diagonal criss-cross wire pattern along its entire length, and further includes multiple eyelets or hooks 62 at one end. A first stent end 64 is flared generally inwardly and a second stent end 66 is contoured both inwardly and outwardly as compared to the central region of the stent. Stent 70 includes a bulbous shape to the wires at one end, eyelets or hoops at the opposite end, and differing numbers of stent crowns at the opposite ends of the stent. Stent 80 includes pocket portions 82 that provide attachment points for the leaflets 84 that are positioned inwardly from the outer diameter of the stent 80. Again, these inwardly located attachment points will reduce the potential for leaflet abrasion and moves the commissure attachment points to an area that that puts less stress on the leaflets. Finally, the pockets 82 provide an area where the suture knots can be positioned so that they do not increase the overall crimp profile of the valve.

Figure 9:
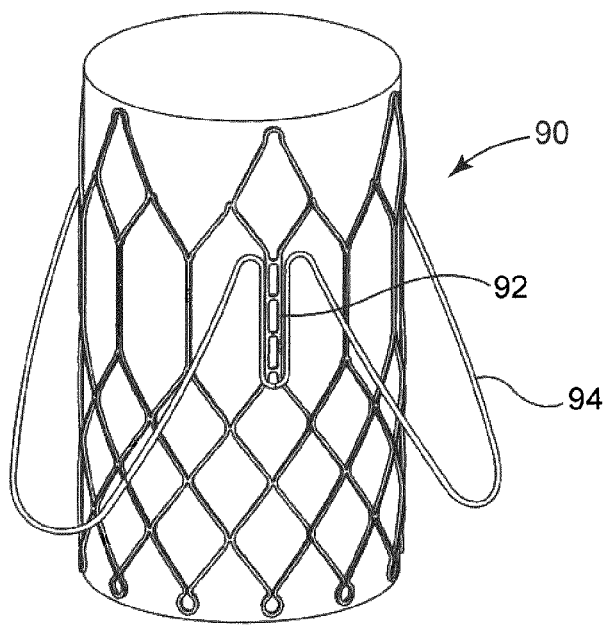
FIG. 9 is a perspective view of a stent embodiment having extending elements and positioned on a mandrel.

FIG. 9 illustrates another stent embodiment 90 that includes several features described above relative to stent crowns, longitudinal posts, incremental steps on at least one of the posts and the wire. Stent 90 also includes at least one longitudinal stent post 92 comprised of two vertical bars spaced from each other. Stent 90 further includes three wings 94, each of which extends outwardly from the stent body and between two longitudinal posts 92. The longitudinal posts 92 can be positioned inwardly of the outer diameter of the stent 90 to provide the advantages discussed above relative to avoiding leaflet abrasion and the like. These wings can be used to dock the stent against the top aspect of the native leaflets when the stent is implanted. Again, this stent has differing numbers of crowns at its opposite ends, and hooks or eyelets on the crowns at one end.

Figure 10:
FIG. 10 is a front view of an exemplary delivery system that can be used for delivering a stent of the type illustrated in FIG. 9.
Figure 12:
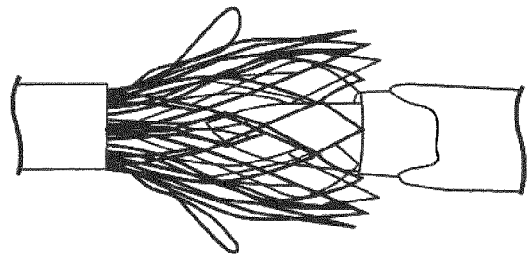
FIG. 11-13 are enlarged front views of a portion of a delivery system for delivering a stent of the type shown in FIG. 9, including three sequential delivery steps.
Figure 11:
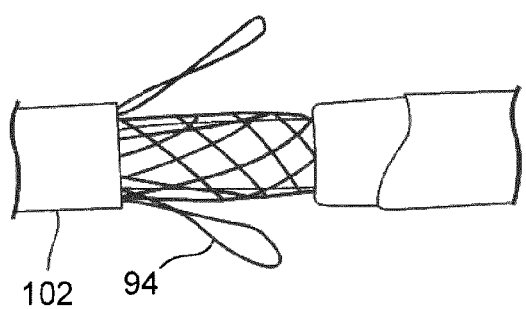
Figure 13:
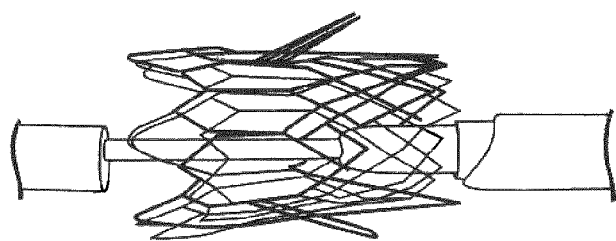

FIGS. 10-13 illustrate a portion of one exemplary delivery system 100 for delivering a stent having wings, such as stent 90. In particular, FIG. 10 shows a delivery system tip including a fully crimped stent enclosed within a main catheter sheath. FIG. 11 shows the wings 94 being deployed from the delivery system 100 by retracting the main catheter sheath 102. In an implantation, the wings 94 can be positioned to interface with the outflow aspect of the native valve leaflets. Once these wings 94 are in contact with the native valve leaflets, the inflow or annular end of the stent is deployed by driving the catheter tip forward, as illustrated in FIG. 12. The native leaflets will now contact the wings 94 and inflow end of the stent 90, thereby minimizing the potential for migration of the replacement valve. The outflow end of the stent can now be deployed, as shown in FIG. 13, to fully re-expand the stent 90 release it from the delivery system, which is accomplished by further retracting the main catheter sheath.

Figure 14:
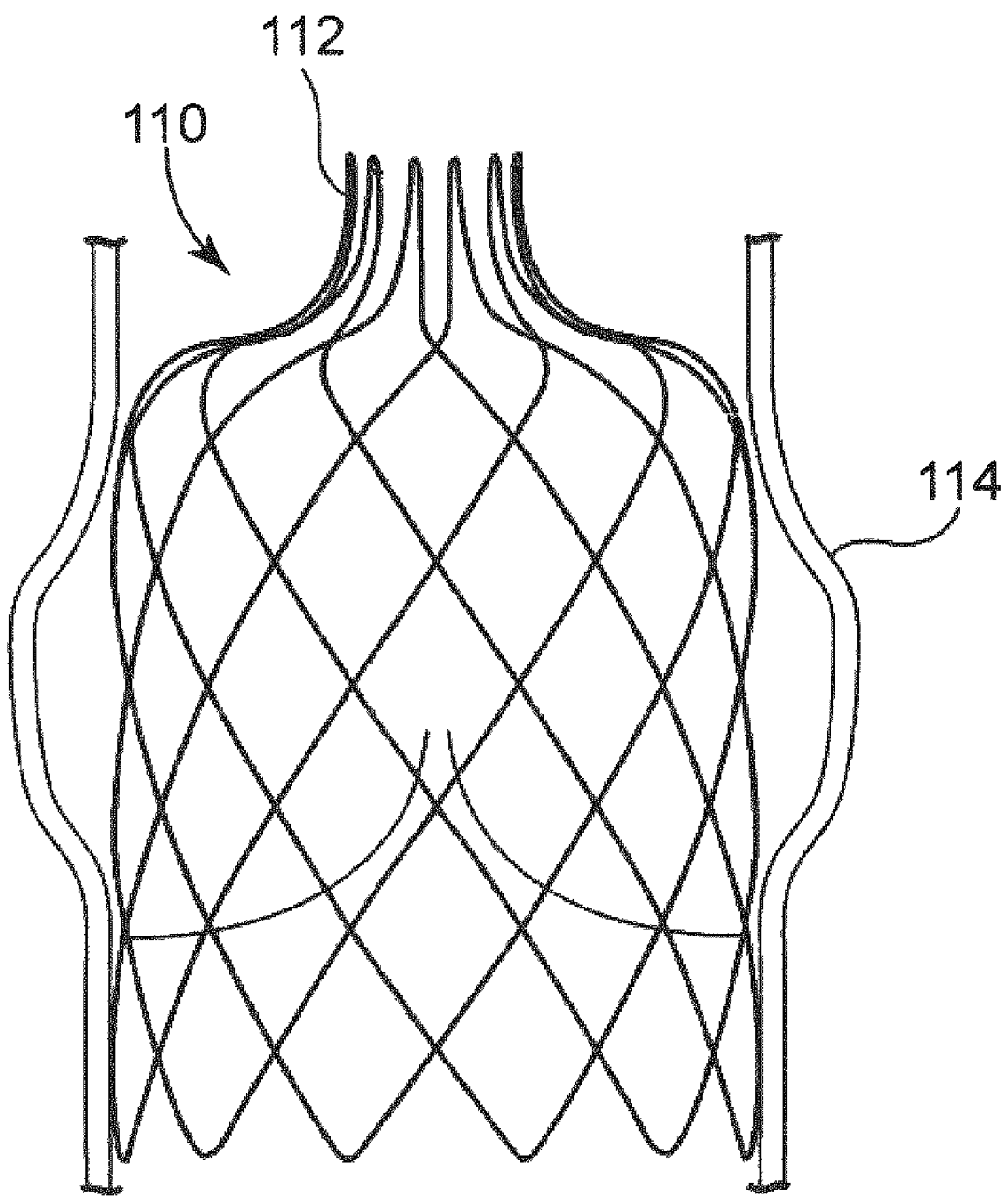
FIG. 14 is a front schematic view of a stent positioned in an aorta.

FIG. 14 illustrates a stent 110 that includes a highly flexible delivery system attachment end 112 that enables the portion of the stent 110 that interfaces with the anatomy to create secure fixation to be fully deployed while still attached to the delivery system. This system enables a sprocket-style delivery system attachment mechanism that can help to minimize the delivery system diameter size. A sprocket-style delivery system includes some type of inner core member from which multiple protrusions extend, where the shape of the protrusions allow for engagement with wires of a stent. Stent 110 does not require attachment of each crown on the aortic end of the stent, while still enabling the ventricular region of the stent to fully deploy to assess functionality and positioning, which can thereby allow for a smaller diameter for the delivery system. As shown, stent 110 is positioned relative to an aorta 114, and stent 110 includes an outflow end that has very flexible struts that enable the anchoring portion of the stent to be fully deployed to assess the valve functionality and positioning, while still being captured on a sprocket-style delivery system. The outer diameter of the stent can preferably expand to match the maximum inner diameter of the anchoring region.

FIG. 15 illustrates another embodiment of a stent 120 having a central region 122 with a diameter that is larger than the diameter at either of the ends. A first end 124 has six stent crowns, while the opposite second end 126 has twelve stent crowns, each of which includes an eyelet 128. With such an arrangement, the number of crowns provided at the outflow end of the stent is reduced, thereby requiring fewer points for attachment to a delivery system. FIG. 16 illustrates another stent embodiment 130 including flared regions at both ends and a central region that is generally cylindrical.

FIG. 17 illustrates another embodiment of a stent 140 that is positioned at the aortic valve position of a heart. Stent 140 includes six stent crowns at one end and twelve stent crowns at the opposite end, and further includes a central area with a relatively large opening or gap 142 between the wires. The gap 142 can be positioned at the coronary ostia so as to not obstruct or interfere with blood flow. The stents 120, 130, 140, along with many of the other stent embodiments described herein, are designed to match with native anatomic features of a patient to improve resistance to migration and improve paravalvular replacement valve sealing.

Figure 18:
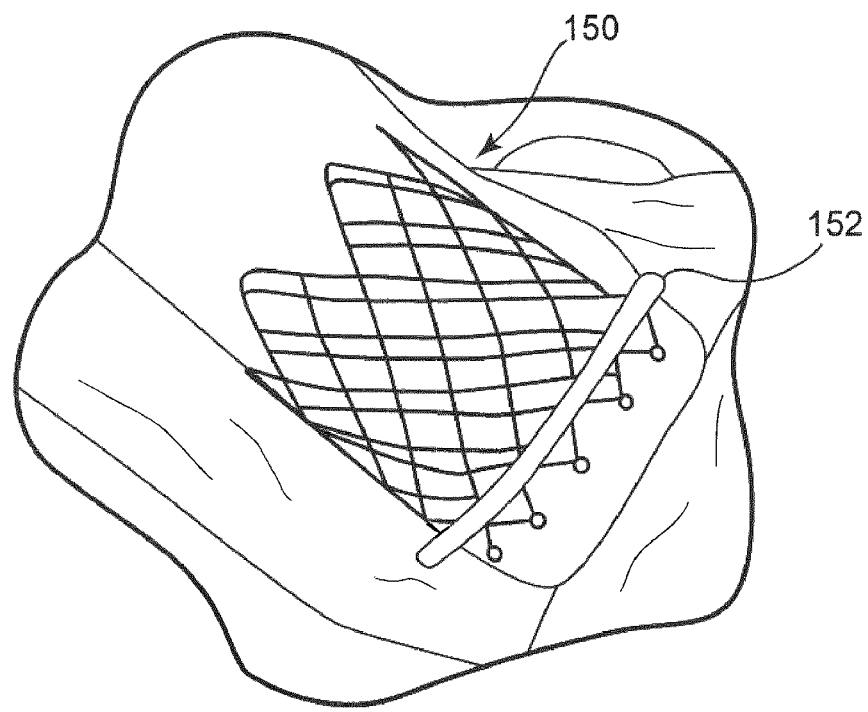

FIG. 18 illustrates another embodiment of a stent 150 that is designed for anatomic compatibility and includes a bulbous portion that is positioned to sit generally at the annular area of a vessel. A ring 152 shown in this figure is a sealing gasket on the outside of the stent and is positioned generally at the annulus of a vessel when implanted. The gasket can be made of fabric or inflatable tube structures, for example.

Figure 19:
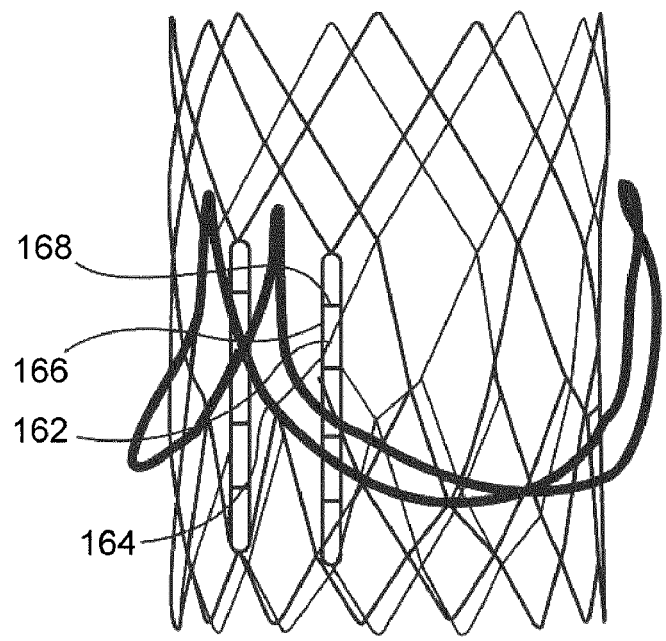
FIG. 19 is a front view of a stent embodiment.

FIG. 19 illustrates a stent 160 that does not include many of the contours described relative to other stent embodiments of the invention, but includes longitudinal posts 162 for attachment of the valve tissue. Posts 162 are comprised of two longitudinal wire portions 166 spaced from each other, and further include optional intermediate members 168 that extend between the longitudinal portions 166. The outer structure ring structure shown in this drawing is provided as an illustration of the general stitching path that can be used for tissue material within the stent.

FIGS. 20-22 illustrate an embodiment of a stent 180 that includes a number of features described above for the stents of the invention, along with additional features. In particular, FIG. 20 shows the stent 180 with longitudinal posts 182 extending in the direction of the length of the stent 180, and a region 184 at one end that is bulbous or has a larger diameter than the central portion of the stent. The opposite end of the stent 180 includes flared portions 186 that extend from opposite sides of the generally tubular central portion. As shown in FIG. 21, each flared portion 186 can include two crowns, although it is possible that the flared portion 186 can be configured somewhat differently than shown (e.g., there can be more or less crowns, the crowns can be shaped differently, the flared portion 186 can extend around a larger or smaller portion of the circumference of the stent, and the like). As is further illustrated in FIG. 20, the geometry of the stent can be designed to incorporate optimal attachment points for tissue. That is, the stent node trajectory can be specifically selected to provide the desired points for the attachment of tissue. Such a feature can be considered and designed for tents including longitudinal posts, as shown in FIG. 20, and may also be considered for stents comprising more diamond-shaped wire patterns without longitudinal posts.

The outer profile of stent 180 is shown in an exemplary position within the anatomy (i.e., aorta) of a patient in FIG. 22, with the central area that includes the commissural posts being positioned in the bulbous area of an aorta. The flares 186 extend into the ventricle in order to help anchor the stent 180 in place. The flares 186 are preferably positioned in locations where they do not disrupt the native anatomical function. That is, the flares 186 should not interfere with the mitral valve anterior leaflet and should not apply pressure to the septum in the area of the conduction system bundle branch. Again, it is also preferable that the central portion of the stent 180 does not contact the native aortic sinus region, in order to minimize the potential for coronary occlusion or obstruction.

It is noted that in many of the stent embodiments shown and described herein, the aspect ratio of certain portions of the stent is exemplary, and can be somewhat different from that shown. It is further noted that if the stent of any of the embodiments is to be positioned to replace the aortic valve, the stent can be provided with a lower density wire portion in the area where the coronaries are located. To eliminate the need to clock the device, reduced wire density around the entire perimeter of the stent in the central area can be provided. Further, stent embodiments described herein may be modified to include additional structure for attachment of tissue for the valve, such as the vertical stent posts described in many of the embodiments.

FIGS. 23-28 illustrate another embodiment of a stent 200 that includes a central cylindrical portion with at least two regions with a lower density of wires, each of which is provided for positioning in the area of the coronary openings. The wires of this lower density area are arranged to provide openings 202 that are larger than the spaces between other wires of the stent. These openings are offset along the length of the stent to be arranged in a zigzag type of pattern around the circumference of the stent 120. One end of the stent 200 includes flared portions 204 that extend from opposite sides of the central cylindrical portion of the stent. Each flared portion 204 includes three crowns, although variations of this configuration are contemplated, as discussed above relative to flared stent portions. As shown in FIG. 26, stent 200 is positioned relative to a mitral valve 210 so that one of the flared portions is positioned at the left ventricle, and one of the openings in the stent is positioned at the left coronary artery. FIG. 27 is a top view of the stent 190, and FIG. 28 shows one exemplary position of the stent 190 relative to the anatomy of a patient, including the septum and anterior leaflet of the mitral valve.

Figure 29:
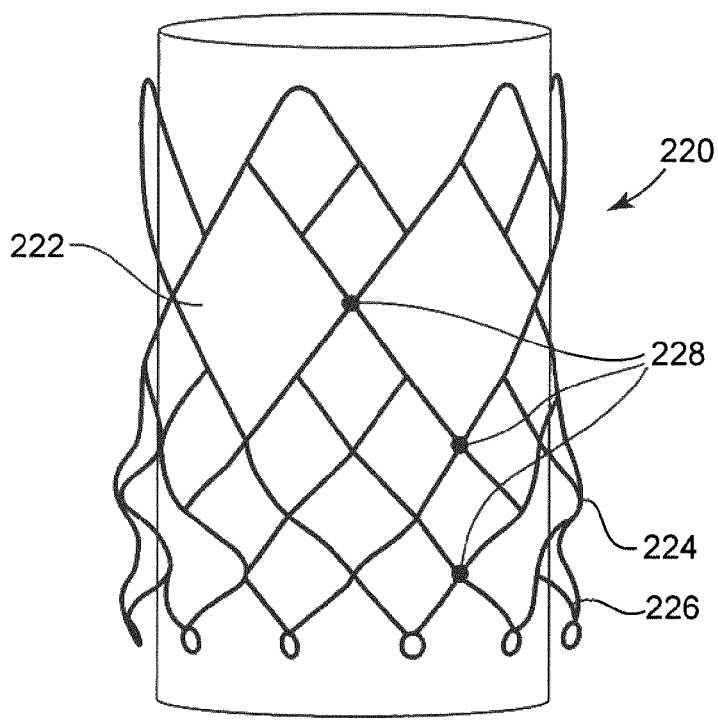
FIG. 29 is a front view of another embodiment of a stent positioned on a mandrel.

FIG. 29 illustrates a stent 220 that includes openings 222 (i.e., areas of lower wire density) for the coronaries, and further includes sub-annular and supra-annular circumferential wings to help secure the stent to the patient's native anatomy. In particular, the area below the openings 222 includes an outward curve or flare to create a wing 224 that can extend around all or part of the circumference of the stent 220. The wires then curve back toward the central longitudinal axis of the stent, then curve or flare outwardly again to create a wing 226 that can extend around all or a part of the circumference of the stent 220. As shown, the wings 224, 226 and the area between them form a generally sinusoidal configuration, where the wing 224 can be positioned above an annulus and wing 226 can be positioned below that annulus to provide the anchoring for a more secure attachment in that position. This series of wings can help to anchor the stent in regions of calcified or fused leaflets in the aortic stenosis patient population. Stent 220 further includes imaging markers 228 that can be used to identify the high and low points of the commissures, the annular (valve) plane of the implant, and/or other features. Markers can also be used to identify high and low boundaries for optimal implant placement within the patient's anatomy.

Figures 30, 31:
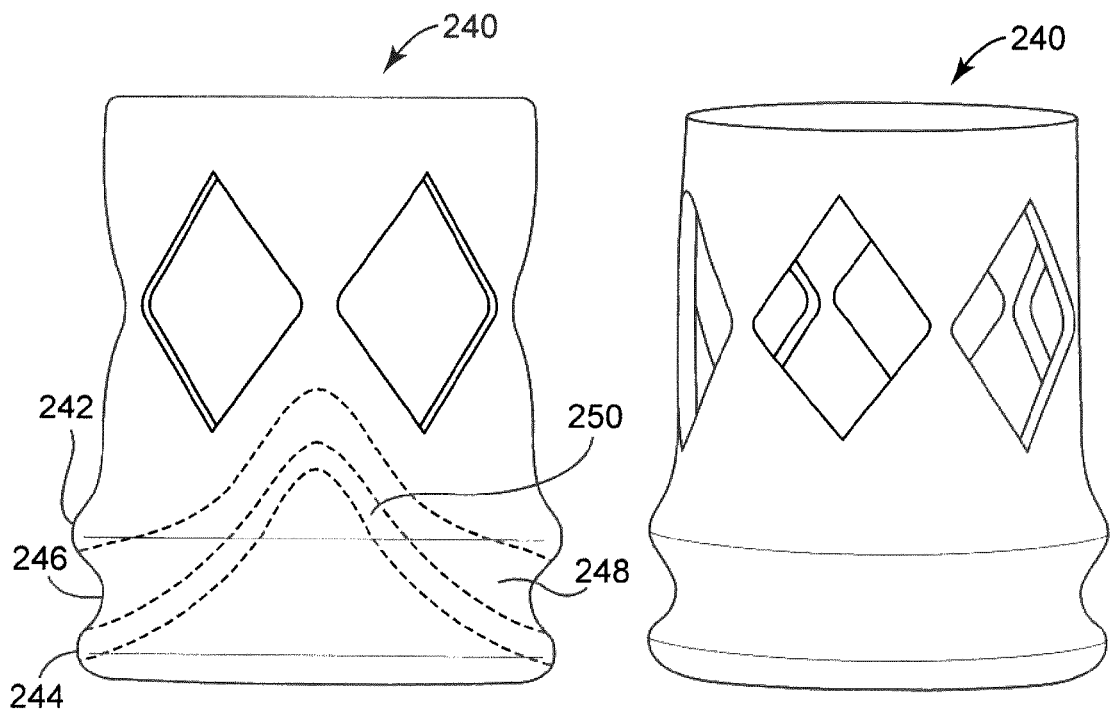
FIGS. 30 and 31 are front and perspective views respectively, of a solid model of a stent of the type illustrated in FIG. 29.

FIGS. 30 and 31 are solid models of a stent 240 that is configured similarly to the stent of FIG. 29, including the sinusoidal shape at one end that creates wing areas. These wings can have a different profile from that shown, although it is preferable in this embodiment that there are sinusoidal "peaks" 242, 244 that are separated by a "valley" 246, where the annulus of a valve can be positioned in the valley 246 so that the peaks 242, 244 are on opposite sides of the annulus. The peaks and valleys can have different heights than shown, and the spacing between the peaks may also be different. That is, the spacing between the sub-annular and supra-annular flares can be varied, depending on the specific procedure that will be performed and the desired characteristics of the stent. These embodiments, along with other shaped stents described herein, can help to minimize stent migration within the patient due to the ability of the stent to conform to various contours of the patient's anatomy. FIG. 30 also illustrates an optional groove 248 that can be positioned generally around the periphery of the stent 240 to match the native 3-dimensional configuration of the native anatomy. A gasket 250 can be positioned within the groove 248, where such a gasket 250 can include one continuous structure that generally follows the shape of the groove 248, or it can include one or more pieces within portions of the groove 248. The gasket 250 can improve paravalvular sealing. Further, the gasket 250 can be made of a material that can heal into the native tissue of the patient, which can help the stent to resist migration.

Figure 32:
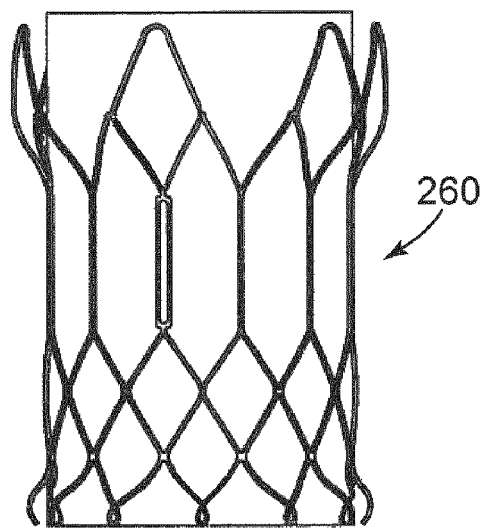
FIGS. 32 and 33 are front perspective views, respectively, of a stent embodiment.
Figure 33:
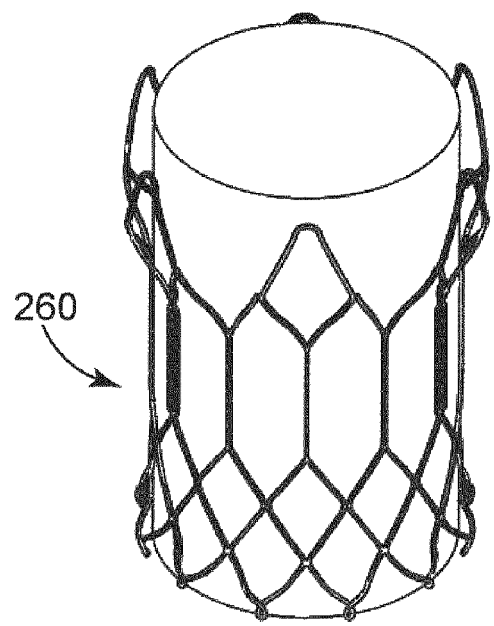

FIGS. 32 and 33 illustrate another stent embodiment 240 that includes flares at both the sub-annular and sinotubular junction (STJ) areas. The illustrated stent further includes vertical stent posts, twelve inflow crowns and six outflow crowns although there could be more or less than these numbers of inflow and outflow crowns. Stent 240 has a wire arrangement similar to that shown for the stents of FIGS. 1-4 and other stents described and shown herein; however, the central area of stent 240 is more tubular or "straight," with slightly curved areas at both ends.

Figure 34:
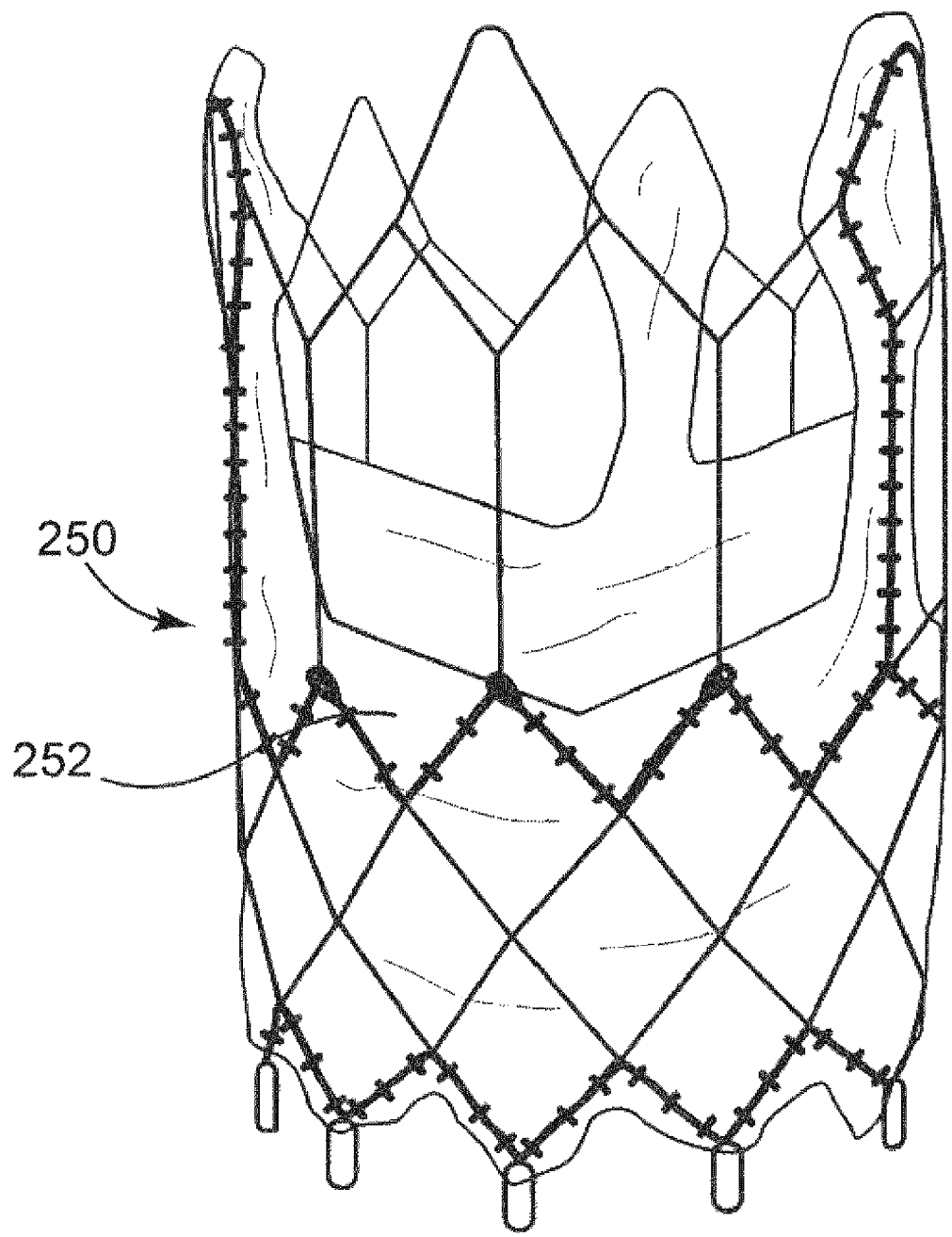
FIGS. 34 and 35 are front views of a valved stent of the invention.
Figure 35:
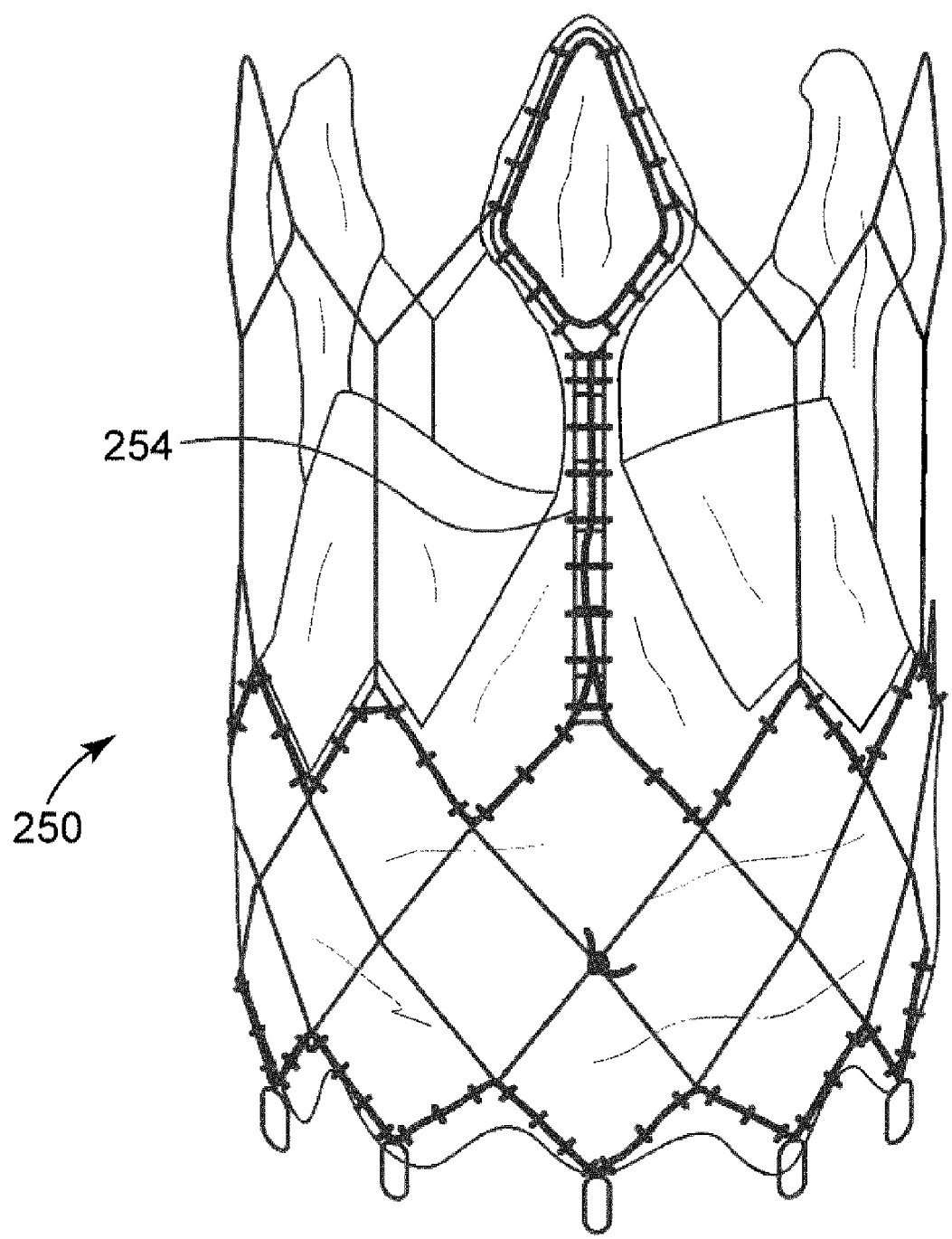

One exemplary stent of the invention combines the following features: eyelets at one end for attachment to the delivery system and tissue valve; vertical commissural tissue attach struts or posts; moderately flared non-commissural attach vertical struts or STJ flare; sub-annular flares; inflow and outflow atraumatic curvatures; a twelve crown inflow; and six tapered crowns at the outflow end. Such an embodiment of a stent is illustrated, for example, as stent 250 in FIGS. 34 and 35. Stent 250 further includes tissue material 252 attached within its internal area to provide leaflets for the valve. Two spaced-apart vertical members are used to make up vertical posts 254, one of which is most visible in FIG. 35. One exemplary pattern for stitching the tissue to the vertical post 254 is also illustrated, although the stitching pattern can differ from that shown.

Delivering any balloon-expandable stents of the invention to the implantation location can be performed percutaneously. In general terms, this includes providing a transcatheter assembly, including a delivery catheter, a balloon catheter, and a guide wire. Some delivery catheters of this type are known in the art, and define a lumen within which the balloon catheter is received. The balloon catheter, in turn, defines a lumen within which the guide wire is slideably disposed. Further, the balloon catheter includes a balloon that is fluidly connected to an inflation source. It is noted that if the stent being implanted is the self-expanding type of stent, the balloon would not be needed and a sheath or other restraining means would be used for maintaining the stent in its compressed state until deployment of the stent, as described herein. In any case, for a balloon-expandable stent, the transcatheter assembly is appropriately sized for a desired percutaneous approach to the implantation location. For example, the transcatheter assembly can be sized for delivery to the heart valve via an opening at a carotid artery, a jugular vein, a sub-clavian vein, femoral artery or vein, or the like. Essentially, any percutaneous intercostals penetration can be made to facilitate use of the transcatheter assembly.

Prior to delivery, the stent is mounted over the balloon in a contracted state to be as small as possible without causing permanent deformation of the stent structure. As compared to the expanded state, the support structure is compressed onto itself and the balloon, thus defining a decreased inner diameter as compared to an inner diameter in the expanded state. While this description is related to the delivery of a balloon-expandable stent, the same basic procedures can also be applicable to a self-expanding stent, where the delivery system would not include a balloon, but would preferably include a sheath or some other type of configuration for maintaining the stent in a compressed condition until its deployment.

With the stent mounted to the balloon, the transcatheter assembly is delivered through a percutaneous opening (not shown) in the patient via the delivery catheter. The implantation location is located by inserting the guide wire into the patient, which guide wire extends from a distal end of the delivery catheter, with the balloon catheter otherwise retracted within the delivery catheter. The balloon catheter is then advanced distally from the delivery catheter along the guide wire, with the balloon and stent positioned relative to the implantation location. In an alternative embodiment, the stent is delivered to an implantation location via a minimally invasive surgical incision (i.e., non-percutaneously). In another alternative embodiment, the stent is delivered via open heart/chest surgery. In one embodiment of the stents of the invention, the stent includes a radiopaque, echogenic, or MRI visible material to facilitate visual confirmation of proper placement of the stent. Alternatively, other known surgical visual aids can be incorporated into the stent. The techniques described relative to placement of the stent within the heart can be used both to monitor and correct the placement of the stent in a longitudinal direction relative to the length of the anatomical structure in which it is positioned.

Once the stent is properly positioned, the balloon catheter is operated to inflate the balloon, thus transitioning the stent to an expanded state. Alternatively, where the support structure is formed of a shape memory material, the stent can self-expand to its expanded state.

One or more markers on the valve, along with a corresponding imaging system (e.g., echo, MRI, etc.) can be used with the various repositionable delivery systems described herein in order to verify the proper placement of the valve prior to releasing it from the delivery system. A number of factors can be considered, alone or in combination, to verify that the valve is properly placed in an implantation site, where some exemplary factors are as follows: (1) lack of paravalvular leakage around the replacement valve, which can be advantageously examined while blood is flowing through the valve since these delivery systems allow for flow through and around the valve; (2) optimal rotational orientation of the replacement valve relative to the coronary arteries; (3) the presence of coronary flow with the replacement valve in place; (4) correct longitudinal alignment of the replacement valve annulus with respect to the native patient anatomy; (5) verification that the position of the sinus region of the replacement valve does not interfere with native coronary flow; (6) verification that the sealing skirt is aligned with anatomical features to minimize paravalvular leakage; (7) verification that the replacement valve does not induce arrhythmias prior to final release; and (8) verification that the replacement valve does not interfere with function of an adjacent valve, such as the mitral valve.

Figure 36:
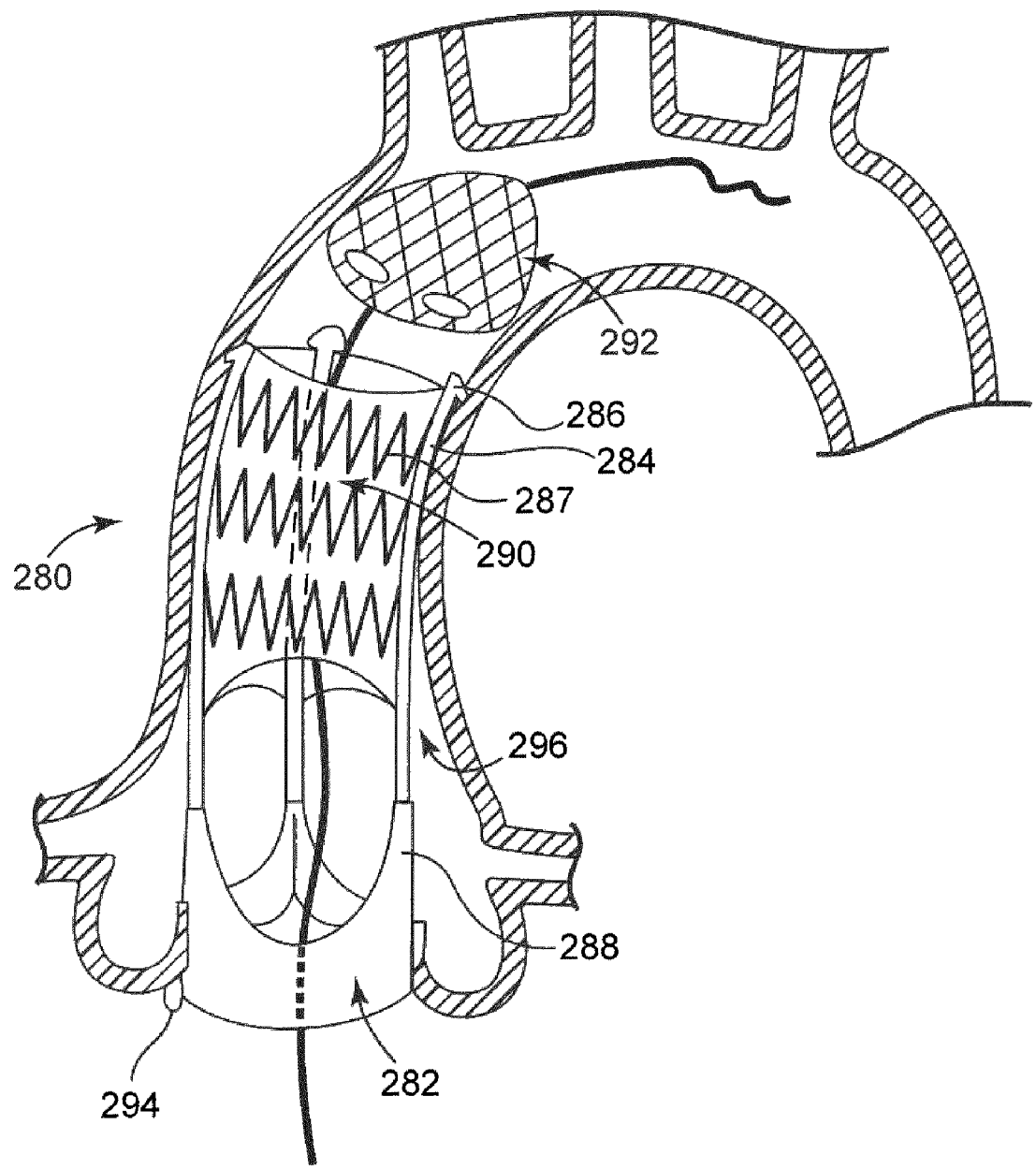
FIG. 36 is a schematic front view of a stent assembly being delivered to a heart valve.

FIGS. 36-39 are schematic views of various embodiments of stents of the present invention. In particular, FIG. 36 illustrates a stent assembly 280 that includes features that align and secure it with specific anatomical features in the left ventricle region and the left ventricular outflow tract region of a patient. Stent assembly 280 includes a stented valve 282 from which tethers 284 extend. Tethers 284 are preferably flexible to accommodate curvature of the native aorta above the valve annulus. Optional anchors 286 are shown at the distal ends of the stent. More specifically, each of the tethers 284 extends from one of the commissures 288 of the stent 282. The stent assembly 280 further includes a distal element such as a stent graft 290 positioned between the tethers 284 near the anchors 286, which is flexible and can accommodate widely varying patient anatomy. The stent graft 290 will be positioned distal to the sinus area of the left ventricular outflow tract when implanted. This configuration can facilitate stabilization of the stent assembly and may be designed to register or interface with another stent graft that is implanted at a later time.

This stent assembly 280 can include flexible connections between annular and supra-annular stent aspects. The flexible connections may be elastomeric, fabric, metal, or the like. Such flexible connections can help the stent assembly to accommodate most varying anatomy above the sinotubular junction and also to accommodate aortic curvature. In addition, the flexible connections can make the stent assembly able to accommodate anerysmal aortas.

The stent assembly 280 may further include a gasket 294 positioned adjacent an end of the stented valve 282. In addition, when the stent assembly is implanted in a patient, a plaque pocket 296 can be created that provides embolic protection by creating a volume that can entrap plaque, calcification, and other emboli from traveling in a distal direction and causing a thromboembolic event, such as a stroke.

Alternatively, portions of the system may be designed to include a longer useful life than others. For example, the frame of the present invention could be designed to have a relatively long useful life (e.g. 20 years), while the tissue component could have a relatively shorter useful life (e.g. 10 years).

An embolic protection device 292 can be provided distal to the stent assembly 280, as is shown in FIG. 36. The device 292 can be utilized during the implantation procedure to capture and trap any emboli released and/or generated by the valve procedure, while still maintaining uninhibited or sufficient perfusion through the aorta and coronary arteries during valve implantation. In addition, FIGS. 36-39 illustrate a portion of the stent positioned above the sinotubular junction 284 covered with fabric, polymer, and/or tissue, which can serve this same purpose.

Figure 37:
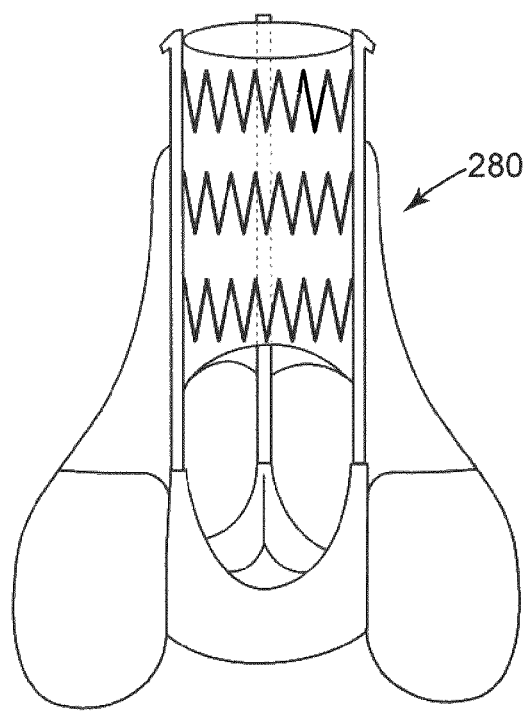
FIG. 37 is a front view of a stent assembly positioned in a heart valve.
Figure 38:
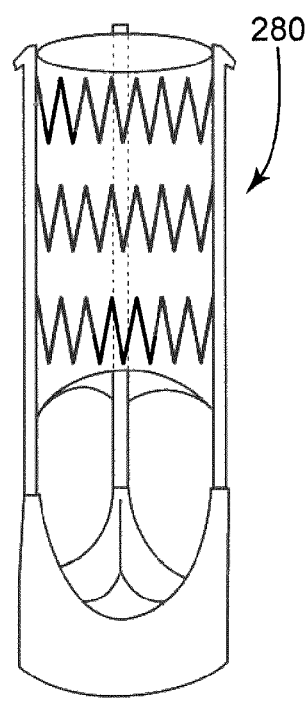
FIG. 38 is a front view of the stent assembly shown in FIGS. 36 and 37.
Figure 39:
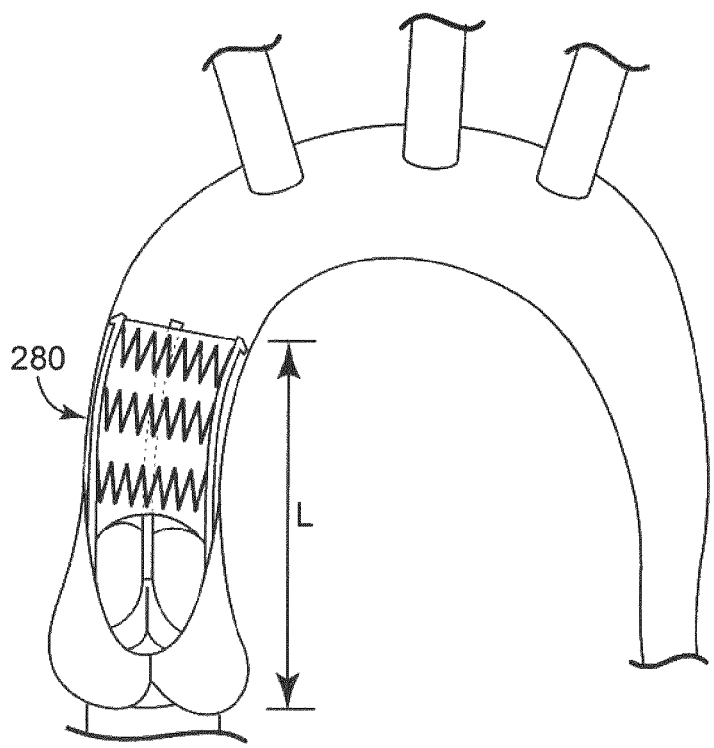
FIG. 39 is a front view of a stent assembly having a length L positioned in a heart vessel.

FIGS. 37-39 illustrate alternative views of the stent assembly 280, both within a heart vessel and independent of anatomical structure (FIG. 38). It is noted that the anchoring of the stent posts via the anchors 286 can help to prevent valve ejection. FIG. 37 shows the stent assembly 280 implanted in a supra-annular position in a patient's anatomy, which can beneficially improve the orifice area by avoiding the stenotic region of the aorta. FIG. 39 shows the flexibility of the stent graft material in order to conform to the curved area of an aorta.

Figure 40:
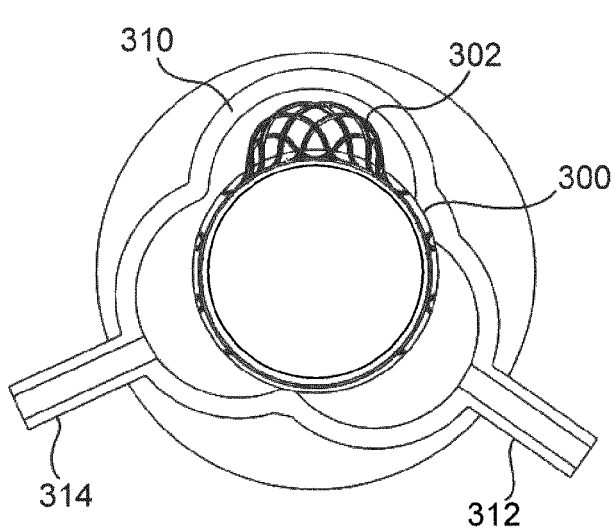
FIG. 40 is a top view of another stent embodiment positioned relative to a schematic view of an anatomical position in a heart.
Figure 42:
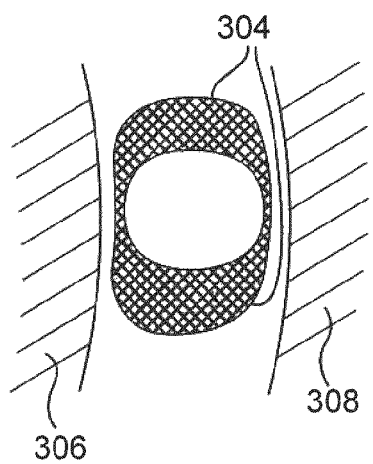
FIG. 42 is a top view of another stent positioned relative to the interventricular septum and the mitral apparatus.
Figure 41:
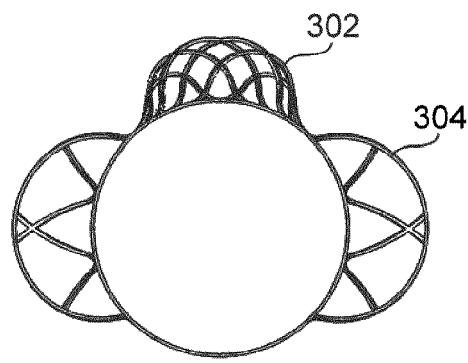
FIG. 41 is a top view of another stent embodiment.

FIG. 40 illustrates a top view of a stent 300 having a fixation tab 302 positioned in the non-coronary sinus area 310, and with no such tabs at either the right coronary artery 314 or the left coronary artery 312. That is, fixation components of stent 300 may secure the system to non-coronary sinus and/or regions of the left ventricle adjacent to the aortic valve annulus. This may avoid obstruction of coronary blood flow and prevent unwanted interaction between the system and the septum and mitral valve anterior leaflet. Further, the fixation tab 302 does not prevent or inhibit subsequent coronary intervention, while providing the advantage of minimizing or preventing migration of the stent toward the aorta. FIG. 41 illustrates a stent having both a fixation tab 302 and flared portions 304 that help to prevent migration of the stent. FIG. 42 illustrates stent 300 having flared regions 304 as positioned relative to the interventricular septum 306 and the mitral valve apparatus 308.

Figure 43:
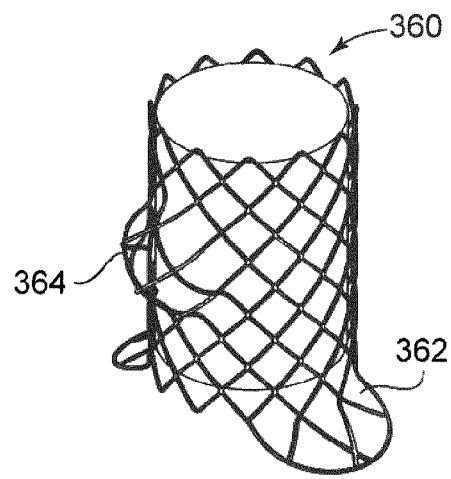
FIGS. 43-45 are perspective views of additional stent embodiments.
Figure 44:
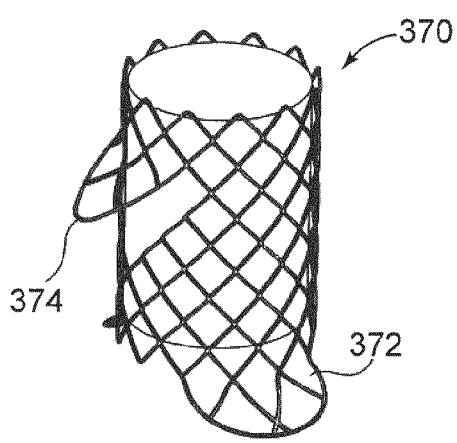
Figure 45:
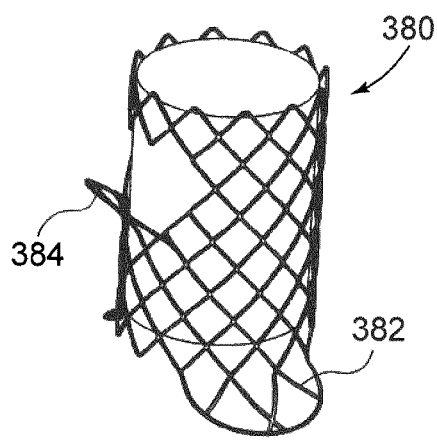
Figure 51:
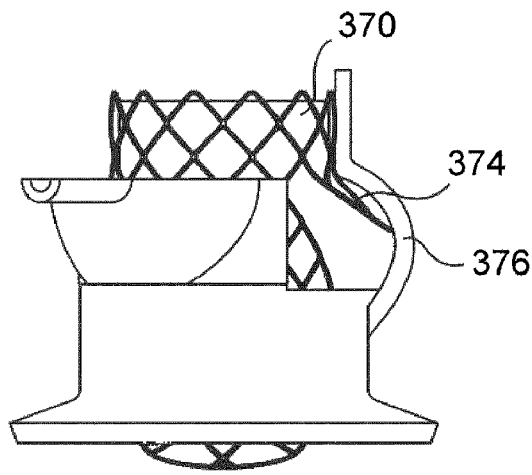
FIGS. 51-53 are front views of a different stents positioned relative to a portion of a heart valve that is cut-away for clarity.
Figure 52:
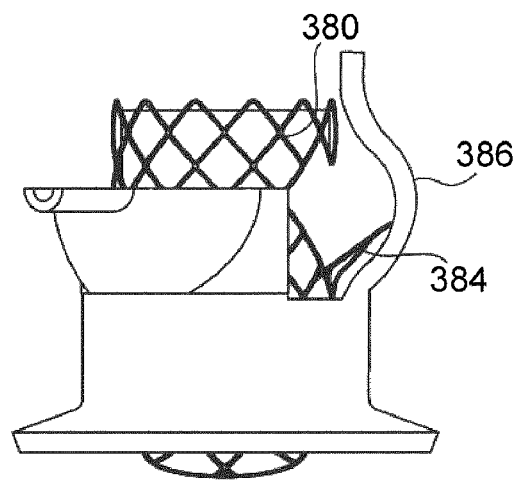
Figure 53:
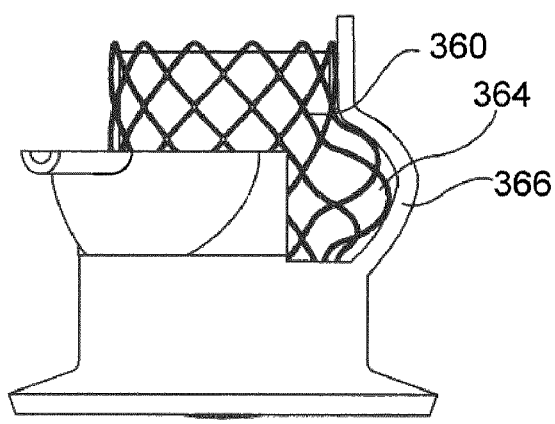

FIGS. 43-45 illustrate alternative stent embodiments 360, 370, 380, each of which comprises an extending or fixation tab 364, 374, 384, respectively, along with flared portions 362, 372, 382, respectively. Tab 364 of stent 360 is configured as a bulging wire area, tab 374 of stent 370 comprises an extension that is angled in the same general direction as the wings 372, and tab 384 of stent 380 comprises an extension that is angle in generally the opposite direction from that of the wings 382. The stent 370 is illustrated in FIG. 51 with its tab 374 positioned relative to a non-coronary sinus 376, stent 380 is illustrated in FIG. 52 with its tab 384 positioned relative to a non-coronary sinus 386, and stent 360 is illustrated in FIG. 53 with its fixation tab 364 positioned relative to a non-coronary sinus 366. As shown, these tabs can help to prevent stent migration due to their interference with the patient's anatomy.

FIGS. 47 and 48 schematically illustrate the aorta of a patient. As shown, the aorta begins to curve distal to the annulus level. Many typical transcatheter valve stents are cylindrical with a relatively straight axis. Such a stent structure does not easily conform to the native anatomy, which can present a number of potential issues. First, the reduced pressure on the anatomy at the inner portion of the curvature (such as is illustrated with the an area 332 adjacent to a stent 330 in FIG. 49) can lead to improper seating, migration, and/or paravalvular leakage. Second, increased pressure on the anatomy at the outer portion of the curvature can lead to, or increase the potential for cardiac conduction system block or interference. Third, increased pressure on the anatomy at the outer portion of the curvature can lead to local erosion, irritation, and/or dissection of tissue. Fourth, the stent can be subjected to increased torsional and/or bending stresses and strains, which can affect the short-term structural integrity of the stent. Finally, lack of conformity with the curvature of the native anatomy can inhibit the ability of the clinician to accurately or consistently position the stent/valve in the desired location.

Several stents of the present invention can alleviate this non-conformity of the valve frame with the native anatomy. In one embodiment, the stent could have a predetermined curvature that matches or more closely conforms to the native anatomy, such as stent 335 in FIG. 50. In other embodiments, the stent could have flexibility (e.g., area 322 of stent 320 in FIGS. 47-48) or a hinged area (e.g., hinge 342 of stent 340 in FIG. 48) in the portion of the stent that would enable it to conform to the native curved anatomy. FIGS. 46 and 47 illustrate stent designs that incorporate flexibility in their central regions, which in turn enables improved conformity with the native anatomy. The central areas or members 322 can be fabricated from a wide variety of materials, such as metals, polymers, fabrics, and the like. The members 322 can include a number of geometries that allow flexibility to conform to the native, curved aortic anatomy. Referring again to FIG. 36, this stent assembly incorporates elements 287 that are not attached to each other except through flexible materials such as fabric, tissue, or polymeric materials that enable a high degree of conformity with the native anatomy curvature within the ascending aorta.

The present invention also optionally or alternatively includes distal emoboli protection features which may be incorporated into a delivery system for delivering a stent assembly (e.g. in the nose assembly), such as the thromboembolic filter. The protection features may provide acute protection during percutaneous valve delivery. The protection features may afford substantially uninhibited flow through coronaries during systole or diastole.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

What is claimed is:

1. A stented valve comprising:
   a stent structure comprising a generally tubular body portion having an interior area, a longitudinal axis, and a plurality of longitudinally extending wires in a central region of the stent structure, wherein the plurality of wires includes multiple commissure wires and at least one structural wire positioned between each two adjacent commissure wires, wherein each of the commissure wires comprises an attachment portion that extends in a generally parallel direction to the longitudinal axis and that is spaced at a first distance from the longitudinal axis, wherein the structural wires are spaced at a second distance from the longitudinal axis, and wherein the first distance is smaller than the second distance; and
   a valve structure comprising a plurality of leaflets, wherein each leaflet comprises a first end, a second end, and a free edge extending between the first and second ends;
   wherein a first end of each leaflet is attached to the attachment portion of one of the commissure wires in the central stent region and a second end of each leaflet is attached to the attachment portion of an adjacent commissure wire in the central stent region so that the free edge of each leaflet does not contact the structural wires in the central stent region when the valve is in an open position.

2. The stented valve of claim 1, wherein one of the first and second ends of the stent structure is curved outwardly relative to the longitudinal axis.

3. A stented valve comprising:
   a stent structure comprising a generally tubular body portion having an interior area, a longitudinal axis, and a plurality of longitudinally extending wires in a central region of the stent structure, wherein the plurality of wires includes multiple commissure wires spaced at a first distance from the longitudinal axis and at least one structural wire positioned between each two adjacent commissure wires, wherein the structural wires are spaced at a second distance from the longitudinal axis, wherein the first distance is smaller than the second distance; and
   a valve structure comprising a plurality of leaflets, wherein each leaflet comprises a first end, a second end., and a free edge extending between the first and second ends;
   wherein a first end of each leaflet is attached to a commissure wire in the central stent region and a second end of each leaflet is attached to an adjacent commissure wire in the central stent region so that the free edge of each leaflet does not contact the structural wires in the central stent region when the valve is in an open position;
   wherein one of the first and second ends of the stent structure is curved inwardly relative to the longitudinal axis.

4. A stented valve comprising:
   a stent structure comprising a generally tubular body portion having a first end and a second end, wherein the diameter at one of the ends is different from the diameter at the second end; and
   a valve structure attached within the generally tubular body portion, wherein a central region of the stent structure between the first and second ends has a diameter than is larger than the diameter of both the first and second ends of the stent structure.

5. A stented valve comprising:
a stent structure comprising a generally tubular body portion having a first end and a second end, wherein an area adjacent the first end has a first stiffness, an area adjacent the second end has a second stiffness, and a central region between the areas at the first and second ends has a third stiffness that is less than the stiffness adjacent the first and second ends, wherein the stent structure can be reconfigured in its central area to match a curved patient anatomical region; and
a valve structure attached within the generally tubular body portion.

6. The stented valve of claim 5, wherein the stent structure comprises a wire structure, and wherein the central region of the stent structure has a lower wire density than a wire density adjacent to the first and second ends of the stent.

7. The stented valve of claim 5, wherein the central region comprises a hinge.

8. The stented valve of claim 5, wherein the central region comprises stent graft material.

9. A stented valve comprising:
a stent structure comprising a generally tubular body portion having a first end and a second end, at least one wing extending outwardly relative to a longitudinal axis of the body portion at the first end of the body portion, and at least one intermediate wing extending outwardly relative to a longitudinal axis of the body portion between its first and second ends, wherein the intermediate wing is positioned for engagement with a non-coronary sinus area of a patient's heart; and
a valve structure attached within the generally tubular body portion,
wherein the intermediate wing comprises a contoured element extending outwardly from the tubular body portion of the stent structure.

10. The stented valve of claim 9, wherein the intermediate wing extends toward a first end of the body portion.

11. The stented valve of claim 9, wherein the intermediate wing extends toward a second end of the body portion.

* * * * *

UNITED STATES PATENT AND TRADEMARK OFFICE
CERTIFICATE OF CORRECTION

| | | |
|---|---|---|
| PATENT NO. | : 7,972,378 B2 | Page 1 of 1 |
| APPLICATION NO. | : 12/321760 | |
| DATED | : July 5, 2011 | |
| INVENTOR(S) | : Charles Tabor et al. | |

It is certified that error appears in the above-identified patent and that said Letters Patent is hereby corrected as shown below:

Patent Column 16 Line 51 Error Reads as "a second end.,";

Correction to Patent should read as "a second end,"

Signed and Sealed this
First Day of November, 2011

David J. Kappos
*Director of the United States Patent and Trademark Office*